(12) United States Patent
Stürzebecher et al.

(10) Patent No.: US 7,838,560 B2
(45) Date of Patent: Nov. 23, 2010

(54) UROKINASE INHIBITORS, PRODUCTION AND USE THEREOF

(75) Inventors: Jörg Stürzebecher, Erfurt (DE); Torsten Steinmetzer, Jena (DE); Andrea Schweinitz, Jena (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 1028 days.

(21) Appl. No.: 10/506,579

(22) PCT Filed: Mar. 11, 2003

(86) PCT No.: PCT/EP03/02489

§ 371 (c)(1), (2), (4) Date: Apr. 13, 2005

(87) PCT Pub. No.: WO03/076391

PCT Pub. Date: Sep. 18, 2003

(65) Prior Publication Data

US 2005/0176993 A1 Aug. 11, 2005

(30) Foreign Application Priority Data

Mar. 11, 2002 (DE) .................. 102 10 592
Sep. 26, 2002 (DE) .................. 102 45 059
Dec. 28, 2002 (DE) .................. 102 61 435

(51) Int. Cl.
*A61K 31/18* (2006.01)
*C07C 323/00* (2006.01)
(52) U.S. Cl. ........................... 514/604; 564/162
(58) Field of Classification Search ............... None
See application file for complete search history.

(56) References Cited

U.S. PATENT DOCUMENTS

| | | | |
|---|---|---|---|
| 5,518,735 A | 5/1996 | Stürzebecher et al. | |
| 5,602,253 A | 2/1997 | Antonsson et al. | |
| 5,705,487 A | 1/1998 | Schacht et al. | |
| 5,707,966 A | 1/1998 | Schacht et al. | |
| 5,710,130 A | 1/1998 | Schacht et al. | |
| 5,726,159 A | 3/1998 | Schacht et al. | |
| 5,786,328 A | 7/1998 | Dennis et al. | |
| 5,863,929 A | 1/1999 | Klimkowski et al. | |
| 5,914,319 A | 6/1999 | Schacht et al. | |
| 6,030,972 A | 2/2000 | Böhm et al. | |
| 6,472,393 B1 | 10/2002 | Aliagas-Martin et al. | |
| 6,586,405 B2 | 7/2003 | Semple et al. | |
| 6,624,169 B1 | 9/2003 | Wilhelm et al. | |
| 6,680,320 B2 | 1/2004 | Wilhelm et al. | |
| 6,831,196 B2 | 12/2004 | Stürzebecher et al. | |
| 6,841,701 B2 | 1/2005 | Stürzebecher et al. | |
| 6,841,702 B2 | 1/2005 | Magdolen et al. | |
| 7,038,074 B2 | 5/2006 | Moroder et al. | |
| 7,049,460 B1 | 5/2006 | Magdolen et al. | |
| 7,208,521 B2 | 4/2007 | Magdolen et al. | |
| 7,342,018 B2 | 3/2008 | Wilhelm et al. | |
| 7,407,982 B2 | 8/2008 | Steinmetzer et al. | |
| 7,538,216 B2 | 5/2009 | Sperl | |
| 7,608,623 B2 | 10/2009 | Sperl et al. | |
| 2004/0087511 A1 | 5/2004 | Shiraishi et al. | |
| 2004/0266766 A1 | 12/2004 | Sperl | |
| 2005/0119190 A1 | 6/2005 | Stürzebecher et al. | |
| 2006/0068457 A1 | 3/2006 | Ziegler et al. | |
| 2006/0148901 A1 | 7/2006 | Stürzebecher et al. | |
| 2007/0055065 A1 | 3/2007 | Stürzebecher et al. | |
| 2007/0066539 A1 | 3/2007 | Stürzebecher et al. | |
| 2008/0261998 A1 | 10/2008 | Sperl et al. | |
| 2009/0117185 A1 | 5/2009 | Steinmetzer et al. | |
| 2010/0022781 A1 | 1/2010 | Steinmetzer et al. | |

FOREIGN PATENT DOCUMENTS

| | | |
|---|---|---|
| CA | 2412181 | 12/2002 |
| CH | 689 611 | 7/1999 |
| DE | 42 43 858 | 6/1994 |
| DE | 100 29 015 | 12/2001 |
| DE | 10029014 A1 | 12/2001 |
| DE | 102 10 590 | 3/2002 |
| DE | 102 12 555 | 9/2003 |
| DE | 103 01 300 | 7/2004 |
| EP | 0 183 271 | 6/1986 |
| EP | 0 669 317 | 8/1995 |
| EP | 0 672 658 | 9/1995 |
| EP | 1 364 960 | 11/2003 |
| WO | WO 92/08709 | 5/1992 |
| WO | WO 94/18185 | 8/1994 |
| WO | WO 94/29336 | 12/1994 |
| WO | WO 95/17885 | 7/1995 |
| WO | WO 95/29189 | 11/1995 |
| WO | WO 96/25426 | 8/1996 |
| WO | WO 97/23499 | 7/1997 |
| WO | WO 99/05096 | 2/1999 |
| WO | WO 00/04954 | 2/2000 |
| WO | WO 00/05245 | 2/2000 |
| WO | WO 00/14110 | 3/2000 |
| WO | WO 00/17158 | 3/2000 |

(Continued)

OTHER PUBLICATIONS

Baker et al., "Inhibition of Cancer Cell Urokinase Plasminogen Activator by Its Specific Inhibitor PAI-2 and Subsequent Effects on Extracellular Matrix Degradation," *Cancer Research* 50:4676-4684 (1990).

(Continued)

*Primary Examiner*—Paul A Zucker
(74) *Attorney, Agent, or Firm*—Clark & Elbing LLP

(57) ABSTRACT

The invention relates to novel inhibitors of urokinase and to their preparation and use for the therapy, prophylaxis and diagnosis of a tumor, in particular for reducing the formation of tumor metastases.

21 Claims, 1 Drawing Sheet

FOREIGN PATENT DOCUMENTS

| WO | WO 00/58346 | 10/2000 |
|---|---|---|
| WO | WO 00/64470 | 11/2000 |
| WO | WO 01/81314 A1 | 11/2001 |
| WO | WO 01/96286 A2 | 12/2001 |
| WO | WO 01/96366 | 12/2001 |
| WO | WO 01/97794 | 12/2001 |
| WO | WO 02/06280 | 1/2002 |
| WO | WO 02/14349 A2 | 2/2002 |
| WO | WO 02/20475 | 3/2002 |
| WO | WO 02/50056 | 6/2002 |
| WO | WO 03/070229 | 8/2003 |
| WO | WO 2004/062657 | 7/2004 |

OTHER PUBLICATIONS

Cajot et al., "Plasminogen-Activator Inhibitor Type 1 is a Potent Natural Inhibitor of Extracellular Matrix Degradation by Fibrosarcoma and Colon Carcinoma Cells," *Proc. Natl. Acad. Sci. USA* 87:6939-6943 (1990).

Dixon, "The Determination of Enzyme Inhibitor Constants," *Biochem. J.* 55:170-171 (1953).

Duggan et al., Urokinase Plasminogen Activator and Urokinase Plasminogen Activator Receptor in Breast Cancer, *Int. J. Cancer* 61:597-600 (1995).

Judkins et al., "A Versatile Synthesis of Amidines from Nitriles Via Amidoximes," *Synthetic Communications* 26:4351-4367 (1996).

Kettner et al., "Inactivation of Trypsin-Like Enzymes with Peptides of Arginine Chloromethyl Ketone," *Methods in Enzymology* 80:826-843 (1981).

Krüger et al., "Host TIMP-1 Overexpression Confers Resistance to Experimental Brain Metastasis of a Fibrosarcoma Cell Line," *Oncogene* 16:2419-2423 (1998).

Krüger et al., "The Bacterial *LacZ* Gene: An Important Tool for Metastasis Research and Evaluation of New Cancer Therapies," *Cancer and Metastasis Reviews* 17:285-294 (1999).

Künzel et al., "4-Amidinobenzylamine-Based Inhibitors of Urokinase," *Biorganic & Medicinal Chemistry Letters* 12:645-648 (2002).

Mignatti et al., "Biology and Biochemistry of Proteinases in Tumor Invasion," *Physiological Reviews* 73:161-195 (1993).

Ossowski et al., "Antibodies to Plasminogen Activator Inhibit Human Tumor Metastasis," *Cell* 35:611-619 (1983).

Pedersen et al., "Prognostic Impact of Urokinase, Urokinase Receptor, and Type 1 Plasminogen Activator Inhibitor in Squamous and Large Cell Lung Cancer Tissue," *Cancer Research* 54:4671-4675 (1994).

Reuning et al., "Multifunctional Potential of the Plasminogen Activation System in Tumor Invasion and Metastasis (Review)," *International Journal of Oncology* 13:893-906 (1998).

Schechter et al., "On the Size of the Active Site in Proteases," *Biochemical and Biophysical Research Communications*, 27:157-162 (1967).

Schmitt et al., "Clinical Impact of the Plasminogen Activation System in Tumor Invasion and Metastasis: Prognostic Relevance and Target for Therapy," *Thrombosis and Haemostasis* 78:285-296 (1997).

Sperl et al., "(4-Aminomethyl) Phenylguanidine Derivates as Nonpeptidic Highly Selective Inhibitors of Human Urokinase," *PNAS* 97:5113-5118 (2000).

Stephens et al., "The Urokinase Plasminogen Activator System as a Target for Prognostic Studies in Breast Cancer," *Breast Cancer Research and Treatment*, 52:99-111 (1998).

Stürzebecher et al., "3-Amidinophenylalanine-Based Inhibitors of Urokinase," *Bioorganic & Medicinal Chemistry Letters* 9:3147-3152 (1999).

Stürzebecher et al., "Synthesis and Structure -Activity Relationships of Potent Thrombin Inhibitors: Piperazides of 3-Amidinophenylalanine," *J. Med. Chem.* 40:3091-3099 (1997).

Stürzebecher et al., "Synthetische Inhibitoren der Serinproteinasen," *Pharmazie* 33:599-602 (1978).

Sucker et al., "Pharm. Techn. 2.," Bauer, Georg Thieme Verlag, Stuttgart, 1991.

Tamura et al., "Synthesis and Biological Activity of Peptidyl Aldehyde Urokinase Inhibitors," *Bioorganic & Medicinal Chemistry Letters* 10:983-987 (2000).

Towle et al., "Inhibition of Urokinase by 4-Substituted Benzo[b]thiophene-2-Carboxamidines: An Important New Class of Selective Synthetic Urokinase Inhibitor," *Cancer Research* 53:2553-2559 (1993).

Vassalli et al., "Amiloride Selectively Inhibits the Urokinase-Type Plasminogen Activator," *FEB* 214:187-191 (1987).

Zeslawska et al., "Crystals of Urokinase Type Plasminogen Activator Complexes Reveal the Binding Mode of Peptidomimetic Inhibitors," *J. Mol.Biol.* 328:109-118 (2003).

Akers, "Excipient-Drug Interactions in Parenteral Formulations." *J. Pharm. Sci.* 91(11):2283-2300 (2002).

Asghar et al., "Human Plasma Kallikreins and Their Inhibition by Amidino Compounds," *Biochim. Biophys. Acta* 438:250-264 (1976).

Bauer, "Hilfsstoffe," in *Pharmazeutische Technologie*. Sucker et al. (eds.), Georg Thieme Verlag Stuttgart: New York, p. 174-216 (1991).

Bookser et al., "Syntheses of Quadruply Two-and Three-Atom, Aza-Bridged, Cofacial Bis (5,10,15,20-Tetraphenylporphyrins)," *J. Am. Chem. Soc.* 113:4208-4218 (1991).

Choi-Sledeski et al., "Discovery of an Orally Efficacious Inhibitor of Coagulation Factor Xa Which Incorporates a Neutral $P_1$ Ligand," *J. Med. Chem.* 46:681-684 (2003).

Collen et al., "In Vivo Studies of a Synthetic Inhibitor of Thrombin," *J. Lab. Clin. Med.* 99:76-83 (1982).

Coussens et al., "Matrix Metalloproteinase Inhibitors and Cancer: Trials and Tribulations," *Science* 295:2387-2392 (2002).

Dexter et al., "*N,N*-Dimethylformamide-induced Alteration of Cell Culture Characteristics and Loss of Tumorigenicity in Cultured Human Colon Carcinoma Cells," *Cancer Res.* 39:1020-1025 (1979).

Enyedy et al., "Structure-Based Approach for the Discovery of Bis-benzamidines as Novel Inhibitors of Matriptase," *J. Med. Chem.* 44:1349-1355 (2001).

Eriksson et al., "The Direct Thrombin Inhibitor Melagatran Followed by Oral Ximelagatran Compared with Enoxaparin for the Prevention of Venous Thromboembolism after Total Hip or Knee Replacement: the EXPRESS study," *Journal of Thrombosis and Haemostasis*, 1:2490-2496 (2003).

Fareed et al., "Inhibition of Serine Proteases by Low Molecular Weight Peptides and Their Derivatives", *Ann. N. Y. Acad. Sci.* 370:765-784 (1981).

Francis et al., "Comparison of Ximelagatran with Warfarin for the Prevention of Venous Thromboembolism after Total Knee Replacement," *N. Engl. J. Med.* 349:1703-1712 (2003).

Frérot et al., "PyBOP® and PyBroP: Two reagents for the Difficult Coupling of the α,α-Dialkyl Amino Acid, Aib," *Tetrahedron*, 47(2):259-270 (1991).

Friedrich et al., "Catalytic Domain Structures of MT-SP1/Matriptase, a Matrix-degrading Transmembrane Serine Proteinase," *J. Biol. Chem.* 277:2160-2168 (2002).

Garrett et al., "Synthesis of Potent and Selective Inhibitors of Human Plasma Kallikrein," *Bioorg. Med. Chem. Lett.* 9:301-306 (1999).

Garrett et al., "Peptide Aldehyde Inhibitors of the Kallikreins: An Investigation of Subsite Interactions with Tripeptides Containing Structural Variations at the Amino Terminus," *J. Pept. Res.* 52:60-71 (1998).

Griffin, "Role of Surface in Surface-Dependent Activation of Hageman Factor (Blood Coagulation Factor XII)", *Proc. Natl. Acad. Sci. USA* 75:1998-2002 (1978).

Gustafsson et al., "Effects of Melagatran, a New Low-Molecular-Weight Thrombin Inhibitor, on Thrombin and Fibrinolytic Enzymes," *Thromb. Haemost.* 79:110-118 (1998).

Gustafsson et al., "Effects of Inogatran, A New Low-Molecular-Weight Thrombin Inhibitor, in Rat Models of Venous and Arterial Thrombosis, Thrombolysis and Bleeding Time," *Blood Coagulation and Fibrinolysis* 7:69-79 (1996).

Gustafsson et al., "The Direct Thrombin Inhibitor Melagatran and Its Oral Prodrug H 376/95: Intestinal Absorption Properties, Biochemical and Pharmacodynamic Effects," *Thromb. Res.* 101:171-181 (2001).

Gustafsson et al., "A New Oral Anticoagulant: The 50-Year Challenge," *Nature Reviews Drug Discovery* 3:649-659, 2004.

Hara et al., "DX-9065a, a New Synthetic, Potent Anticoagulant and Selective Inhibitor for Factor Xa," *Thromb. Haemost.* 71:314-319 (1994).

Herbert et al., "DX 9065A, a Novel, Synthetic, Selective and Orally Active Inhibitor of Factor Xa: In Vitro and In Vivo Studies," *J. Pharmacol. Exp. Ther.* 276:1030-1038 (1996).

Ho et al., "Exploratory Solid-Phase Synthesis of Factor Xa Inhibitors: Discovery and Application of $P_3$-Heterocyclic Amides as Novel Types of Non-Basic Arginine Surrogates," *Bioorg. Med. Chem. Lett.* 9:3459-3464 (1999).

Hooper et al., "Type II Transmembrane Serine Proteases," *J. Biol. Chem.* 276:857-860 (2001).

Ihara et al., "Prometastatic Effect of N-Acetylglucosaminyltransferase V is Due to Modification and Stabilization of Active Matriptase by Adding β1-6 GlcNAc Branching," *J. Biol. Chem.* 277:16960-16967 (2002).

Isobe, "Inhibitory Effect of Gabexate (FOY) on Contact System," *Blood & Vessel* 12:135-138 (1981).

Kang et al., "Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer," *Cancer Res.* 63:1101-1105 (2003).

Kaplan, "Initiation of the Intrinsic Coagulation and Fibrinolytic Pathways of Man: The Role of Surfaces, Hageman Factor, Prekallikrein, High Molecular Weight Kininogen, and Factor XI," *Prog. Hemostasis Thromb.* 4:127-175 (1978).

Kettner et al., "The Selective Inhibition of Thrombin by Peptides of Boroarginine," *J. Biol. Chem.* 265, 18289-18297 (1990).

Kettner et al., "The Selective Affinity Labeling of Factor $X_a$ by Peptides of Arginine Chloromethyl Ketone," *Thromb. Res.* 22:645-652 (1981).

Kim et al., "Preparation of Argatroban Analog Thrombin Inhibitors with Reduced Basic Guanidine Moiety, and Studies of Their Cell Permeability and Antithrombotic Activities," *Med. Chem. Res.* 377-383 (1996).

Kirk, "4-Lithio-1-Tritylimidazole as a Synthetic Intermediate. Synthesis of Imidazole-4-Carboxaldehyde," *J. Heterocyclic Chem.* 22:57-59 (1985).

Lawson et al., "Studies on the Inhibition of Human Thrombin: Effects of Plasma and Plasma Constituents,"*Folia Haematol, Leipzig* 109, 52-60 (1982).

Leadley, "Coagulation Factor Xa Inhibition: Biological Background and Rationale," *Curr. Topics in Med. Chem.*, 1:151-159 (2001).

Lee et al., "Noncovalent Tripeptidic Thrombin Inhibitors Incorporating Amidrazone, Amine and Amidine Functions at P1," *Bioorg. Med. Chem. Lett.* 12:1017-1022 (2002).

Lee et al., "Noncovalent Thrombin Inhibitors Incorporating an Imidazolylethynyl P1," *Bioorganic & Medicinal Chemistry Letters*, 10:2775-2778 (2000).

Lee et al., "Activation of Hepatocyte Growth Factor and Urokinase/Plasminogen Activator by Matriptase, an Epithelial Membrane Serine Protease," *J. Biol. Chem.* 275:36720-36725 (2000).

Lin et al., "Characterization of a Novel, Membrane-bound, 80-kDa Matrix-degrading Protease from Human Breast Cancer Cells," *J. Biol. Chem.* 272:9147-9152 (1997).

Lin et al., "Molecular Cloning of cDNA for Matriptase, a Matrix-degrading Serine Protease with Trypsin-like Activity," *J. Biol. Chem.* 274:18231-18236 (1999).

Lin et al., "Purification and Characterization of a Complex Containing Matriptase and a Kunitz-type Serine Protease Inhibitor from Human Milk," *J. Biol. Chem.* 274:18237-18242 (1999).

Long et al., "Synthesis and Evaluation of the Sunflower Derived Trypsin Inhibitor as a Potent Inhibitor of the Type II Transmembrane Serine Protease, Matriptase," *Bioorg. Med. Chem. Lett.* 11:2515-2519 (2001).

Maduskuie el al., "Rational Design and Synthesis of Novel, Potent Bis-Phenylamidine Carboxylate Factor Xa Inhibitors," *J. Med. Chem.* 41:53-62 (1998).

Maignan et al., "The Use of 3D Structural Data in the Design of Specific Factor Xa Inhibitors," *Curr. Topics in Med. Chem.* 1:161-174 (2001).

Mohan et al., "Solid-Phase Synthesis of N-Substituted Amidinophenoxy Pyridines as Factor Xa Inhibitors," *Bioorg. Med. Chem. Lett.* 8:1877-1882 (1998).

Morrissette et al., "Low Molecular Weight Thrombin Inhibitors With Excellent Potency, Metabolic Stability, and Oral Bioavailability," *Bioorganic & Med. Chem. Letters*, 14:4161-4164 (2004).

Muramatu et al., "Inhibitory Effects of ω-Amino Acid Esters on Trypsin, Plasmin, Plasma Kallikrein and Thrombin," *Biochim. Biophys. Acta* 242:203-208 (1971).

Muramatu et al., "Inhibitory Effects of ω-Guanidino Acid Esters on Trypsin, Plasmin, Plasma Kallikrein and Thrombin," *Biochim. Biophys. Acta* 268:221-224 (1972).

Muramatu et al., "Inhibitory Effects of Aryl *trans*-4 (Aminomethyl) Cyclohexanecarboxylate on Serine Proteases, and their Antiallergic Effects," *Hoppe-Seyler's Z. Physiol. Chem.* 363:203-211 (1982).

Nar et al., "Structural Basis for Inhibition Promiscuity of Dual Specific Thrombin and Factor Xa Blood Coagulation Inhibitors," *Structure*, 9:29-37 (2001).

Nelson et al., "Stereoselective Synthesis of a Potent Thrombin Inhibitor by a Novel P2-P3 Lactone Ring Opening," *J. Org. Chem.* 69:3620-3627 (2004).

Oberst et al., "Expression of the Serine Protease Matriptase and Its Inhibitor HAI-1 in Epithelial Ovarian Cancer: Correlation with Clinical Outcome and Tumor Clinicopathological Parameters," *Clin. Cancer Res.* 8:1101-1107 (2002).

Ohno et al., "FOY: [Ethyl-(6-Guanidinohexanoyloxy) Benzoate] Methanesulfonate as a Serine Proteinase Inhibitor. I. Inhibition of Thrombin and Factor Xa in Vitro," *Thromb. Res.* 19:579-588 (1980).

Okada et al., "Development of Plasmin and Plasma Kallikrein Selective Inhibitors and their Effect on M1 (Melanoma) and HT29 Cell Lines," *Bioorg. Med. Chem. Lett.* 10:2217-2221 (2000).

Okada et al., "Development of Plasma Kallikrein Selective Inhibitors," *Biopolymers* 51:41-50 (1999).

Okamoto et al., "Recent Studies of the Synthetic Selective Inhibitors; With Special Reference to Non-Plasmin Fibrinolytic Enzyme, Plasmin and Plasma-Kallikrein," *Thromb. Res., Suppl. I*, 131-141 (1988).

Ostrem et al., "Discovery of a Novel, Potent, and Specific Family of Factor Xa Inhibitors via Combinatorial Chemistry," *Biochemistry* 37:1053-1059 (1998).

Patani et al., "Bioisosterism: A Rational Approach in Drug Design." *Chem. Rev.* 96:3147-3176 (1996), pp. 3147-3148 and 3170.

Pauls et al., "The Design of Competitive, Small-Molecule Inhibitors of Coagulation Factor Xa," *Frontiers in Med. Chem.*, 1:129-152 (2004).

Perzborn et al., "In Vitro and In Vivo Studies of the Novel Antithrombotic Agent BAY 59/7939—an Oral, direct Factor Xa Inhibitor," *J. Thromb. & Haemost.* 3:514-521 (2005).

Phillips et al., "Discovery of N-[2-[5-[Amino(imino)methyl]-2-hydroxyphenoxy]-3,5-difluoro-6-[3-(4,5-dihydro-1-methyl-1H-imidazol-2-yl)phenoxy]pyridin-4-yl]-N-methylglycine (ZK-807834): A Potent, Selective, and Orally Active Inhibitor of the Blood Coagulation Enzyme Factor Xa," *J. Med. Chem.* 41:3557-3562 (1998).

Quan et al., "Bisbenzamidine Isoxazoline Derivatives as Factor Xa Inhibitors," *Bioorg. Med. Chem. Lett.* 7:2813-2818 (1997).

Quan et al., "Discovery of 1-(3'-Aminobenzisoxazol-5'-yl)-3-trifluormethyl-*N*-[2-fluoro-4-[(2'-dimethylaminomethyl)imidazol-1-yl]phenyl]-1*H*-pyrazole-5-carboxyamide Hydrochloride (Razaxaban), a Highly Potent, Selective, and Orally Bioavailable Factor Xa Inhibitor," *J. Med. Chem.* 48:1729-1744 (2005).

Quan et al., "The Race to Orally Active Factor Xa Inhibitor: Recent Advances," *Curr. Opin. In Drug Discovery & Development*, 7:460-469 (2004).

Ratnoff, "Studies on the Inhibition of Ellagic Acid-Activated Hageman Factor (factor XII) and Hageman factor fragments," *Blood* 57:55-58 (1981).

Renatus et al., "Structural and Functional Analyses of Benzamidine-based Inhibitors in Complex with Trypsin: Implications for the Inhibition of Factor Xa, tPA, and Urokinase." *J. Med. Chem.* 41:5445-5456 (1998).

Rittle et al., "Unexpected Enhancement of Thrombin Inhibitor Potency with o-Aminoalkylbenzylamides in the P1 Position," *Bioorg. Med. Chem. Lett.* 13:3477-3482 (2003).

Robinson et al., "Chapter 9. Anticoagulants: Inhibitors of the Factor VIIa/Tissue Factor Pathway,"*Ann. Rep. Med. Chem.* 37:85-94 (2002).

Rubini et al., "Synthesis of Isosteric Methylene-oxy Pseudopeptide Analogues as Novel Amide Bond Surrogate Units." *Tetrahedron* 43(21):6039-6045 (1986).

Sato et al., "Antithrombotic Effects of YM-60828, a Newly Synthesized Factor Xa Inhibitor, in Rat Thrombosis Models and Its Effects on Bleeding Time," *Br. J. Pharmacol.* 123:92-96 (1998).

Sato et al., "YM-60828, a Novel Factor Xa Inhibitor: Separation of Its Antithrombotic Effects from Its Prolongation of Bleeding Time," *Eur. J. Pharmacol.* 339:141-146 (1997).

Satoh et al., "Medicinal Chemical Studies on Synthetic Protease Inhibitors, trans-4-Guanidinomethylcyclohexanecarboxylic Acid Aryl Esters," *Chem. Pharm. Bull.* 33:647-654 (1985).

Shi et al., "Identification and Characterization of a Novel Matrix-degrading Protease from Hormone-dependent Human Breast Cancer Cells," *Cancer Res.* 53:1409-1415 (1993).

Silverberg et al., "Enzymatic Activities of Activated and Zymogen Forms of Human Hageman Factor (Factor XII)," *Blood* 60:64-70 (1982).

Soll et al., "Amidinohydrazones as Guanidine Bioisosteres: Application to a New Class of Potent, Selective and Orally Bioavailable, Non-Amide-Based Small Molecule Thrombin Inhibitors," *Bioorganic & Medicinal Chemistry Letters* 10:1-4 (2000).

Sperl et al., "Urethanyl-3-Amidinophenylalanine Derivatives as Inhibitors of Factor Xa. X-Ray Crystal Structure of a Trypsin/Inhibitor Complex and Modeling Studies," *Biol. Chem.* 381:321-329 (2000).

Stauffer et al., "9-Hydroxyazafluorenes and Ttheir Use in Thrombin Inhibitors," *J. Med. Chem.*, 48: 2282-2293 (2005).

Stürzebecher et al., "Novel Plasma Kallikrein Inhibitors of the Benzamidine Type," *Brazilian Journal Med. Biol. Res.* 27:1929-1934 (1994).

Stürzebecher et al., "Synthesis and Structure -Activity Relationships of Potent Thrombin Inhibitors: Piperazides of 3-Amidinophenylalanine," *J. Med. Chem.* 40:3091-3099 (1997).

Stürzebecher et al., "Synthetic Inhibitors of Bovine Factor Xa and Thrombin Comparison of Their Anticoagulant Efficiency," *Thromb. Res.* 54:245-252 (1989).

Stürzebecher et al., *Zentralbl. Pharm. Pharmakother. Lab. Diagn.* 122:240-241 (1983).

Tada et al., "Isolation of Plasma Kallikrein by High Efficiency Affinity Chromatography and Its Characterization," *Biol. Pharm. Bull.* 24:520-524 (2001).

Takeuchi et al., "Reverse Biochemistry: Use of Macromolecular Protease Inhibitors to Dissect Complex Biological Processes and Identify a Membrane-type Serine Protease in Epithelial Cancer and Normal Tissue," *Proc. Natl. Acad. Sci. USA* 96:11054-11061 (1999).

Takeuchi et al., "Cellular Localization of Membrane-type Serine Protease 1 and Identification of Protease-activated Receptor-2 and Single-chain Urokinase-type Plasminogen Activator as Substrates," *J. Biol. Chem.* 275:26333-26342 (2000).

Teno et al., "Development of Selective Inhibitors against Plasma Kallikrein," *Chem. Pharm. Bull.* 39:2930-2936 (1991).

Tucker et al., "Potent Noncovalent Thrombin Inhibitors That Utilize the Unique Amino Acid d-Dicyclohexylalanine in the P3 Position. Implications on Oral Bioavailability and Antithrombotic Efficacy," *J. Med. Chem.* 40:1565-1569 (1997).

Tucker et al., "Synthesis of a Series of Potent and Orally Bioavailable Thrombin Inhibitors That Utilize 3,3-Disubstituted Propionic Acid Derivatives in the $P_3$ Position," *J. Med. Chem.* 40:3687-3693 (1997).

Tsuda et al., "Structure-Inhibitory Activity Relationship of Plasmin and Plasma Kallikrein Inhibitors," *Chem. Pharm. Bull.* 49:1457-1463 (2001).

von der Saal et al, "Derivatives of 4-Amino-Pyridine as Selective Thrombin Inhibitors," *Bioorganic & Medicinal Chemistry Letters* 7:1283-1288 (1997).

Wagner et al., "Synthese von N-[Amidinobenzyl]-und N-[Amidinophenylj-Phthalimide und-1-Oxoisoindoline," *Pharmazie* 32:76-79 (1977).

Weitz, "New Anticoagulants for Treatment of Venous Thromboembolism," *Circulation*, 110:I-19-I-26 (2004).

Wikström et al., "Development and Validation of a Chiral Capillary Electrophoresis Method for Melagatran and Ximelagatran Drug Substances," *J. Sep. Sci.* 25:1167-1174 (2002).

Zeslawska et al., "Crystals of the Urokinase Type Plasminogen Activator Variant βc-uPA in Complex with Small Molecule Inhibitors Open the Way Towards Structure-based Drug Design," *J. Mol. Biol.* 301:465-475 (2000).

Zhang et al., "Assignment of Human Putative Tumor Suppressor Genes ST13 (alias SNC6) and ST14 (alias SNC19) to Human Chromosome Bands 22q13 and 11q24→q25 by In Situ Hybridization," *Cytogenet. Cell Genet.* 83:56-57 (1998).

Zhu et al., "Recent Advances in Inhibitors of Factor Xa in the Prothrombinase Complex," *Curr. Opin. Cardiovasc. Pulmon. Renal Invest. Drugs* 1:63-87 (1999).

Office Action pertaining to U.S. Appl. No. 10/297,557 mailed Nov. 4, 2003.

Office Action pertaining to U.S. Appl. No. 10/311,364 mailed Nov. 19, 2003.

Office Action pertaining to U.S. Appl. No. 10/311,364 mailed Apr. 1, 2004.

Office Action pertaining to U.S. Appl. No. 10/540,958, mailed Nov. 17, 2008.

Office Action pertaining to U.S. Appl. No. 10/540,958, mailed Jun. 11, 2009.

Office Action pertaining to U.S. Appl. No. 10/555,821, mailed Jan. 21, 2009.

Office Action pertaining to U.S. Appl. No. 10/571,026, mailed Dec. 13, 2007.

Office Action pertaining to U.S. Appl. No. 10/571,026, mailed Feb. 23, 2009.

Office Action pertaining to U.S. Appl. No. 10/571,026, mailed Oct. 30, 2009.

US 7,838,560 B2

UROKINASE INHIBITORS, PRODUCTION AND USE THEREOF

CROSS REFERENCE TO RELATED APPLICATIONS

This application is the U.S. National Stage of International Application No. PCT/EP2003/002489, filed Mar. 11, 2003, which claims benefit of German patent applications 10261435.0, 10245059.5, and 10210592.8 filed Dec. 28, 2002, Sept. 26, 2002 and Mar. 11, 2002, respectively.

The invention relates to novel inhibitors of urokinase and to their preparation and use for the therapy, prophylaxis and diagnosis of a tumor, in particular for reducing the formation of tumor metastases.

The spreading and metastasis of solid tumors in surrounding tissue is made possible by the ability of the tumors to break down the extracellular matrix in the environment of the tumor cell or to penetrate the basal membrane. Aside from a variety of matrix metalloproteinases and cathepsins, it is in particular the plasminogen activator urokinase (uPA) which is of central importance in this process (P. Mignatti and D. B. Rifkin, Physiol. Rev. 73, 161-195, 1993). Thus, uPA activates plasminogen; the plasmin which is formed is able to break down the components of the extracellular matrix (fibrin, fibronectin, laminin and proteoglycans, inter alia) and also activate metalloproteases and prourokinase to form uPA (U. Reuning et al., Int. J. Oncol. 13, 893-906, 1998).

Both prourokinase and uPa bind to the uPA receptor (uPAR), which is a specific receptor which is located on the cell surface. This thereby augments and focuses the activity of uPA, and thus plasminogen activation, in the direct environment of the tumor cell. The importance of this cell-associated plasminogen activator system for tumor growth and spreading has been demonstrated both in cell-biological studies and in animal models. Thus, inhibition of the enzymic activity of uPA by the natural inhibitors PAI-1 and PAI-2 reduces the invasive potential of tumor cells (J.-F. Cajot et al., Proc. Natl. Acad. Sci. USA 87, 6939-6943, 1990; M. Baker et al., Cancer Res. 50, 4876-4684, 1990). In chick embryos, the formation of lung metastases brought about by human carcinoma cells was almost completely prevented by adding antibodies directed against uPA (L. Ossowski et al., Cell 35, 611-619, 1983).

The factors of the plasminogen activator system (uPA, UPAR, PAI-1 and PAI-2) have been intensively investigated in recent years in regard to their clinical relevance for the prognosis of patients possessing solid malignant tumors. In particular, the content of uPA in the tissue of different tumors has proved to be a prognosis factor. Thus, patients having a high uPA level have a worse prognosis than patients with a low concentration of uPA in the tumor (M. Schmitt et al., Thromb. Haemost. 78, 285-296, 1997; R. W. Stephens et al., Breast Cancer Res. Treat. 52, 99-111, 1998). An elevated concentration of uPAR in the tumor tissue also correlates with a poor prognosis (H. Pedersen et al., Cancer Res. 54, 4671-4675, 1994; C. Duggan et al., Int. J. Cancer 61, 597-600, 1995).

It can be assumed, from the findings regarding the prognostic value of the uPA content and uPAR content in tumor tissue, that synthetic uPA inhibitors will be able to suppress invasion by, and spread of, tumor cells. However, the number of previously known uPA inhibitors is relatively small. The majority only possess low specificity and potency, as in the case with various benzamidine and β-naphthamidine derivatives (J. Stürzebecher and F. Markwardt, Pharmazie 33, 599-602, 1978). While the amiloride described by Vassalli and Belin (FEBS Letters 214, 187-191, 1997) as being a uPA inhibitor is indeed a specific inhibitor of uPA, it is only a weak one ($K_i$=7 μM).

4-Substituted benzothiophene-2-carboxamidines have been found to be more strongly active uPA inhibitors ($K_i$=0.16 μM in the case of compound B-623). Inhibitors of this type also inactivate uPA which is bound to uPAR (M. J. Towle et al., Cancer Res. 53, 2553-2559, 1993). The benzothiophene derivatives are very specific; their inhibitory effect on plasmin and tissue-type plasminogen activator (tPA) is low. However, it is a very elaborate matter to synthesize compounds of this type.

4-Aminomethylphenylguanidine derivatives, whose inhibitory effect on uPA ($K_i$=2.4 μM in the case of the most active compound) is, however, comparatively slight, have a comparable specificity (S. Sperl et al., Proc. Natl. Acad. Sci. USA 97, 5113-5118, 2000).

By contrast, Nα-triisopropylphenylsulfonyl-3-amidinophenylalanine derivatives achieve micromolar $K_i$ values (0.41 μM in the case of the most active compound) but are very nonspecific uPA inhibitors, inhibiting trypsin, thrombin and plasmin to the same degree or more powerfully (J. Stürzebecher et al., Bioorg. Med. Letters 9, 3147-3152, 1999). WO 99/05096 and WO 01/81314 disclose very active uPA inhibitors in the form of improved β-naphthamidines. While $IC_{50}$ values in the nanomolar region are reported, no data are provided on selectivity and biological activity.

Thus far only a few peptides derived from the substrate sequence have been reported to be uPA inhibitors. Kettner and Shaw (Methods in Enzymology, 80, 826-842, 1981) describe chloromethyl ketones which, while inhibiting uPA irreversibly, are not suitable for in vivo use.

EP 18 32 71 discloses lysine derivatives which, while having a certain inhibitory effect on uPA, also inhibit other comparable enzymes and can consequently only be used for medicinal purposes in a very specific or restricted manner. The same applies to the low molecular weight polypeptides (approx. 50 amino acids) which are described in WO 95/17885 as being uPA inhibitors and which are derived from natural inhibitors. Their peptide character and their molecular size greatly restrict their use in vivo. WO 00/05245 recently disclosed peptidyl aldehydes which contain an arginal C-terminally and a D-serine in P3 and which inhibited uPA very effectively. Following acylation of the D-Ser hydroxyl, the key compound iBuOCO-D-Ser-Ala-Arg-H was observed to have a relative bioavailability of 87% after s.c. administration (S. Y. Tamura et al. Bioorg. Med. Chem. Lett. 10, 983-987, 2000). PCT/EP WO 01/96286 discloses inhibitors which are derived from acylated amidinobenzylamine and, in addition to a natural amino acid in P2, contain a D-serine, or a comparable unnatural amino acid, in P3. Compounds of this type inhibit urokinase ($K_i$=36 nM in the case of the most active compound) very effectively. However, compounds of this type only possess pharmacokinetic properties which are inadequate for any use in vivo; they are only absorbed to a very limited extent following oral administration and, in experimental animals, are eliminated very rapidly from the circulation following i.v. administration (Künzel et al., Bioorg. Med. Chem. Lett. 12, 645-648 (2002)). WO 01/14349 describes further noncovalently binding urokinase inhibitors which, aside from the acylated amidinobenzylamines which were already described in WO 01/96286, possess, for example, acylated guanidinobenzylamine, 2-amidino-5-aminomethylthiophene and other arginine mimetics as the P1 residue.

The invention is therefore based on the object of specifying an active compound which inhibits urokinase with a high degree of activity, which is also suitable for therapeutic applications and which, after having been administered i.v. or s.c., circulates in the body for as long as possible.

It has been found, surprisingly, that acylated amidinobenzylamine in accordance with the general formula I in patent claim 1

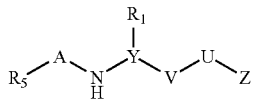

wherein

A is $P_2$—$P_1$ in which

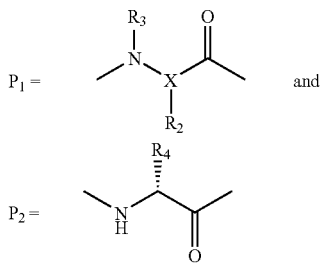

in particular compounds of 4-amidinobenzylamine in which X, $R_2$, $R_3$ and $R_4$ are natural and/or unnatural amino acids, both inhibit urokinase very effectively and are eliminated slowly from the circulation, in particular following i.v. or s.c. administration, when, in addition to the amidino function, other charged groups, preferably carboxyl, amino, amidino, hydroxyamidino, amidrazono or guanidino are introduced. The carboxyl groups can also be protected in the form of their esters, with ethyl esters being preferably used. Some of these esters are converted in vivo into the free acids.

That which has been said above applies, in the same way, to acylated guanidinobenzylamine.

The designation of the residues $P_2$ and $P_1$ in the structural segment A of the general formula I does not refer to the nomenclature, which is otherwise customarily employed, of the amino acid residues in peptide substrates of serine proteases and inhibitors derived therefrom, as was introduced by Schechter and Berger (Schechter and Berger, Biochem. Biophys. Res. Comm. 27, 157-162 (1967)). The following definitions apply in all sections of the invention, i.e. both in the description and in the claims:

The letter P in connection with a number from 1 to 3 in normal script, i.e. P1, P2 or P3, is used for amino acid residues and their derivatives, corresponding to the nomenclature of Schechter and Berger. On the other hand, the letter P in connection with a subscript 1 or 2, i.e. $P_1$ or $P_2$, stands for amino acid residues and their derivatives as constituents of the structure A in formula I of the present invention. In this connection, the substituted or unsubstituted natural or unnatural amino acid $P_1$ in structure A, which amino acid is present in the L configuration, corresponds to P2 in accordance with Schechter and Berger, and the substituted or unsubstituted natural or unnatural amino acid P2 in structure A, which amino acid is present in the D configuration, corresponds to P3 in accordance with Schechter and Berger.

In formula I, $R_1$ is an H or —$(CH_2)_a COOR_6$, in which a=0, 1, 2, 3, 4 or 5, preferably in which a=0, 1 or 2, where $R_6$ is a branched or unbranched alkyl radical preferably having from 1 to 6 C atoms, in particular from 1 to 3 C atoms, especially ethyl;

$R_2$ is an H, a branched or unbranched alkyl radical having from 1 to 8 C atoms, preferably having from 1 to 3 C atoms, or —$(CH_2)_c COOR_8$, in which c=1, 2, 3 or 4, where $R_8$ is H or a branched or unbranched alkyl radical preferably having from 1 to 6 C atoms, in particular from 1 to 3 C atoms, especially ethyl, or —$(CH_2)_d$—$OR_9$, in which d=1, 2, 3 or 4, where $R_9$ is H, or —$(CH_2)_e$—$OR_{10}$, —$(CH_2)_e$—$SR_{10}$, —$(CH_2)_e$-guanidino, —$(CH_2)_e$-imidazole or —$(CH_2)_e NHR_{10}$, in which e=1, 2, 3, 4 or 5, where $R_{10}$ is H, a branched or unbranched alkyl radical having 1-16, in particular 1-8, especially 1-3, C atoms, or a substituted or unsubstituted aryl, heteroaryl, aralkyl or heteroaralkyl radical, where the alkyl radical preferably possesses from 1 to 16, in particular from 1 to 8, especially from 1 to 3, C atoms, and the aryl or heteroaryl radical preferably possesses from 4 to 14, in particular from 6 to 10, especially 6, C atoms, and preferably from 1 to 3 N as heteroatom, or —$(CH_2)_k O$—$CO$—$OR_{16}$, in which k=1, 2, 3, 4, 5, 6, 7 or 8, where $R_{16}$ is a branched or unbranched alkyl having 1-16, preferably 1-8, in particular 1-4, especially 1-2, C atoms, a substituted or unsubstituted aryl, heteroaryl, aralkyl or heteroaralkyl radical, or an adamantyl, a camphor or a cyclohexylmethyl radical, preferably benzyl;

$R_3$ is an H or —$(CH_2)_b R_7$, in which b=1, 2, 3, 4, 5, 6, 7 or 8, preferably in which b=2 or 3, where $R_7$ is H, a branched or unbranched alkyl radical having from 1 to 10 C atoms, preferably having from 1 to 3 C atoms, or a charged radical, preferably a —$(CH_2)_j COOR_{13}$, —$(CH_2)_j SO_2 R_{13}$, or —$(CH_2)_j NH_2$, or —$(CH_2)_j$-amidino, —$(CH_2)_j$-hydroxyamidino or —$(CH_2)_j$-guanidino group in which j=0, 1 or 2, where $R_{13}$ is H or an alkyl radical preferably having from 1 to 6 C atoms, in particular from 1 to 4, especially ethyl;

$R_4$ is a branched or unbranched alkyl radical having from 1 to 8, preferably from 1 to 3, C atoms, —$(CH_2)_f OR_{11}$, —$(CH_2)_f SR_{11}$, or —$(CH_2)_f NHR_{11}$ in which f=1, 2, 3, 4, 5, 6, 7 or 8, where $R_{11}$ is H or —CO—$OR_{17}$, where $R_{17}$ is a branched or unbranched alkyl having 1-16, preferably 1-8, in particular 1-4, especially 1-2, C atoms, a substituted or unsubstituted aryl, heteroaryl, aralkyl or heteroaralkyl radical, or an adamantyl, a camphor or a cyclohexylmethyl radical, preferably benzyl;

$R_5$ is —$(CH_2)_g (CH_3)_h$, —$(CH_2)_i$-aryl, in which g+h=0, 1, 2 or 3, —$SO_2 R_{12}$, —$COR_{12}$ or —$COOR_{12}$, where $R_{12}$ is a branched or unbranched alkyl having 1-16, preferably 1 to 8, in particular 1 to 4, especially 1 to 2, C atoms, a substituted or unsubstituted aryl, heteroaryl, aralkyl or heteroaralkyl radical, or an adamantyl, a camphor or a cyclohexylmethyl radical, preferably benzyl, where $R_5$ can be modified with a charged or uncharged group, preferably a —$(CH_2)_j COOR_{13}$, —$(CH_2)_j SO_2 R_{13}$, —$(CH_2)_j NH_2$, —$(CH_2)_j$-amidino, —$(CH_2)_j$-hydroxyamidino or —$(CH_2)_j$-guanidino group in which j=0, 1 or 2, where $R_{13}$ is H or an alkyl radical preferably having from 1 to 6 C atoms, in particular ethyl;

U is a phenyl or cyclohexyl radical or a heterophenyl or heterocyclohexyl radical preferably having at least one N, S or O as heteroatom, in particular pyridine, piperidine or pyrimidine;

V is $(CH_2)_n$ in which n is 0, 1, 2 or 3, preferably 0;

X is N or CH, preferably CH;

Y is N or $(CH)_m$ in which m=0 or 1, preferably CH;

Z occurs in the 3 or 4 position and is an aminomethyl, a guanidino or an amidino group

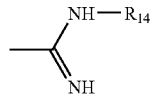

where $R_{14}$ is H, OH, $NH_2$, —$COR_{15}$ or —$COOR_{15}$, where $R_{15}$ is a branched or unbranched alkyl radical having from 1 to 16, preferably from 1 to 8, in particular from 1 to 4, especially from 1 to 2, C atoms or a substituted or unsubstituted aryl or heteroaryl, aralkyl or heteroaralkyl radical, where the alkyl radical preferably possesses from 1 to 16, in particular from 1 to 8, especially from 1 to 4, and particularly preferably from 1 to 2, C atoms and the aryl or heteroaryl radical preferably possesses from 4 to 14, in particular from 6 to 10, especially 6, C atoms and, preferably, from 1 to 3 N as heteroatom;

where one or more charged radicals, preferably derived from —COOH, —CH(COOH)2, —$SO_2$H or $NH_2$, or an amidino, hydroxyamidino, amidrazono or guanidino group, is/are present in the radicals $R_1$, $R_2$, $R_3$ or $R_5$;

preference is also given to a compound of the general formula I in the form of a prodrug or in the form of its salt.

Within the meaning of the present invention, a prodrug is an acylated amidinobenzylamine or guanidinobenzylamine in accordance with the general formula I which is present as a pharmaceutically inactive derivative of the corresponding pharmaceutically active substance and, after having been administered orally, is biotransformed spontaneously or enzymically, with the pharmaceutically active substance being released.

Other particularly preferred inhibitors of the urokinase which are eliminated particularly slowly are 4-amidinobenzylamine derivatives in accordance with the general formula I in which an amino group-functionalized or carboxyl group-functionalized oligo- or polyalkylene glycol chain, in particular a poly- or oligoethylene glycol chain or poly- or oligopropylene glycol chain, is additionally coupled directly to a functional group of $R_2$, in particular by way of an —NH or a —CO group, with the formation of an amide bond at $R_2$, with the oligo- or polyalkylene glycol chain possessing a functional group, in particular a substituted or unsubstituted amino group and/or carboxyl group, at least at both ends, or with the oligo- or polyalkylene glycol chain possessing a functional group, in particular a substituted or unsubstituted amino group and/or carboxyl group, at one end and being present, at the other end, as an alkyl ether having 1-4 C atoms, in particular as methyl ether, with $R_2$ preferably being —$(CH_2)_n$—$NH_2$ in which n is 1-5, preferably 4, or —$(CH_2)_n$—COOH in which n is 1-5, preferably 1-3.

Two molecules of the general formula I can be coupled to an oligo- or polyalkylene glycol chain which possesses a functional group, in particular a substituted or unsubstituted amino group and/or carboxyl group, at least at both ends.

If the derivatives, according to the invention, of 4-amidinobenzylamine are coupled to an oligo- or polyalkylene glycol chain, P1, in the structure A of the general formula I, preferably has the following general formula II:

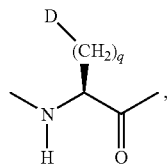

(II)

where q is 0, 1, 2, 3, 4 or 5 and D is formula III $$E-F-G-$$ (III)

where, when E is an $H_2N$, HOOC—$(CH_2)_n$—CO—NH, HOOC, $H_2N$—$(CH_2)_n$—NH—CO or HS group, F is an oligo- or polyalkylene glycol of the general formula —$(CH_2)_d$—[O—$CH_2$—$CH_2$]$_v$O—$(CH_2)_m$—(NH—CO—$CH_2$—O—$CH_2)_k$— or —$(CH_2)_d$—[O—$CH(CH_3)$—$CH_2$]$_v$O—$(CH_2)_m$—(NH—CO—$CH_2$—O—$CH_2)_k$—, in which d=1, 2, 3 or 4, v=an integer from 1 to 1000, preferably from 2 to 250, m=0, 1, 2, 3 or 4, and k=0 or 1, or, when E is a $CH_3$—O group, F is an oligo- or polyalkylene glycol chain of the general formula —$(CH_2)_d$—[O—$CH_2$—$CH_2$]$_v$O—$(CH_2)_m$—(NH—CO—$CH_2$—O—$CH_2)_k$— or —$(CH_2)_d$—[O—$CH(CH_3)$—$CH_2$]$_v$—O—$(CH_2)_m$—(NH—CO—$CH_2$—O—$CH_2)_k$—, in which d=1, 2, 3 or 4, v=an integer from 1 to 1000, preferably from 1 to 250, m=0, 1, 2, 3 or 4, and k=0 or 1; and G is —CO—NH— or —NH—CO—.

A particular advantage of oligo- and/or polyalkylene glycol derivatives of the urokinase inhibitors according to the invention lies in their extended half-life in the circulation following systemic administration.

Other particularly suitable compounds are compounds according to the general formula I in which U is preferably substituted, at 1, 2 or 3 positions, by a halogen, in particular fluorine or chlorine, or a methyl, ethyl, propyl, methoxy, ethoxy or propoxy radical.

Other particularly suitable compounds are compounds according to the general formula I in which a carboxyl group is protected as an ester, preferably as an ethyl ester.

Other particularly suitable compounds are compounds according to the general formula I or II in which the compound is present in the form of a prodrug in which $R_9$ and/or $R_{11}$ is/are, in this case, an alkylcarbonyl, aralkylcarbonyl, alkyloxycarbonyl or aralkyloxycarbonyl radical, with the linear or branched alkyl radical preferably possessing from 1 to 6, in particular from 1 to 4, C atoms and the aryl radical preferably possessing from 5 to 8, in particular 6, C atoms.

Other particularly preferred compounds are compounds according to the general formula I or II in which, in the amidinobenzylamide radical, the amidino group is in position 4 and $P_2$ is derived from the amino acid D-Ser and $P_1$ is derived from glycine, alanine, serine, aspartic acid or glutamic acid and $R_5$ is an unsubstituted or carboxyl group-provided aryl- or aralkylsulfonyl radical having from 1 to 16, preferably from 1 to 8, in particular from 1 to 4, especially from 1 to 2, C atoms in the alkyl radical and from 6 to 14, preferably from 6 to 10, in particular 6, C atoms in the aryl radical.

Other particularly suitable compounds are compounds of the general formula I or II in which, in the amidinobenzylamide radical, the amidino group is in position 4 and $P_2$ is the amino acid D-Ser and $P_1$ is a natural or artificial, unsubstituted or substituted basic amino acid in the L configuration, for example Lys, homoLys, Arg, norArg, homoArg, His, Orn, Orn(2-imidazolinyl), Dab, 4-[(2-amino)pyrimidinyl]butyric acid, Dap, Ala[3-(2-pyrrolidinyl)], Ala[3-pyrrolidinyl-(2-N-amidino)], Ala[3-(N-piperazine-4-N-amidino], Ala(4-Pip), Ala[4-Pip(N-amidino)], homoAla(4-Pip), Ala[3-Pip(N-amidino)], homoAla(3-Pip), homoAla[4-Pip(N-amidino)], Ala-(3-guanidino), Phe(3-amidino), Phe(4-amidino), Phe(3-$NH_2$), Phe(4-$NH_2$), Phe(3-guanidino), Phe(4-guanidino), Phe[4-(2-imidazolinyl)], Phe[3-$CH_2$-(guanidino)], Phe[4-$CH_2$-(guanidino)], homoPhe(3-amidino), homoPhe(4-amidino), hPhe(3-$NH_2$), hPhe(4-$NH_2$), hPhe(3-guanidino), hPhe(4-guanidino), cis-Cha(4-$NH_2$), trans-Cha(4-$NH_2$), cishomoCha(4-NH$_2$), trans-homoCha(4-NH$_2$), trans-Cha(4-CH$_2$NH$_2$) and trans-homoCha(4-CH$_2$NH$_2$), and where R$_5$ is a sulfonyl group-provided aryl- or aralkylsulfonyl radical having from 1 to 16, preferably from 1 to 8, in particular from 1 to 4, especially from 1 to 2, C atoms in the alkyl radical and from 6 to 14, preferably from 6 to 10, in particular 6, C atoms in the aryl radical, which is bonded to the amino group of the D-Ser, with P$_1$ very particularly preferably being the amino acid lysine or arginine.

Other particularly suitable compounds are compounds according to the general formula I or II in which the substituent at the substituted aryl, heteroaryl, aralkyl or heteroaralkyl radical is a halogen, preferably fluorine, chlorine or bromine, in particular fluorine or chlorine.

Other particularly suitable compounds are compounds according to the general formula I or II in which a compound of the general formula I has the following structure:

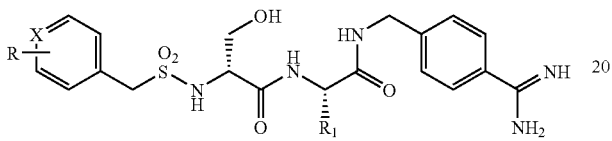

in which R is COOH or COOMe in ortho, meta or para, or H, and X is CH and R$_1$ is H; or
R is 4-COOH or 3-COOH, with X being CH and R$_1$ being H, CH$_3$ or CH$_2$—OH; or
R is 4-CN, with X being CH and R$_1$ being CH$_3$; or
R is 4-(NH$_2$—CH$_2$), with X being CH and R$_1$ being H; or
R is H, with X being CH and R$_1$ being H, CH$_2$—OH, CH$_2$—O(Bzl), CH$_2$—NH$_2$, CH(OH)CH$_3$ or CH(OBzl)CH$_3$; or
R is 4-COOMe, with X being CH and R$_1$ being CH$_2$—OH; or
R is 4-CL, 4-Me, 4-F or 3,4-di-Cl, with X being CH and R$_1$ being H; or
R is H, with X being N and R$_1$ being H.

Other particularly suitable compounds are compounds according to the general formula I or II where a compound of the general formula I possesses one of the following structures:

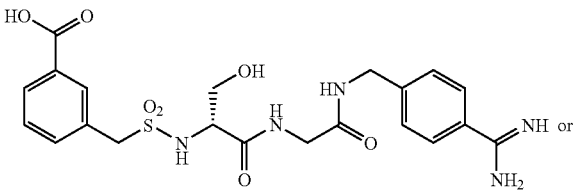

Other particularly suitable compounds are compounds according to the general formula I or II where a compound of the general formula I or II possesses one of the following structures:

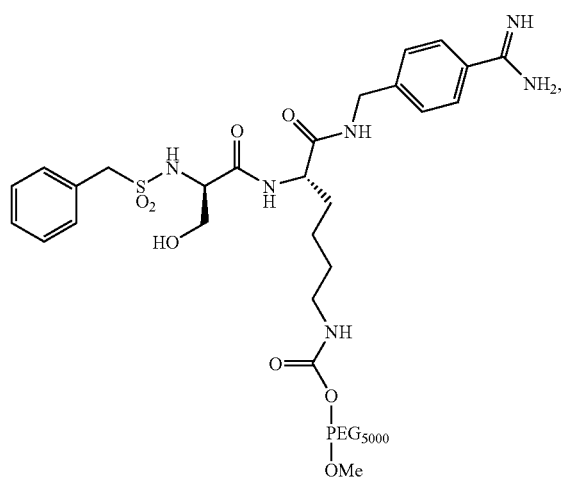

Other particularly suitable compounds are compounds according to the general formula I or II where a compound of the general formula I or II possesses one of the following structures:

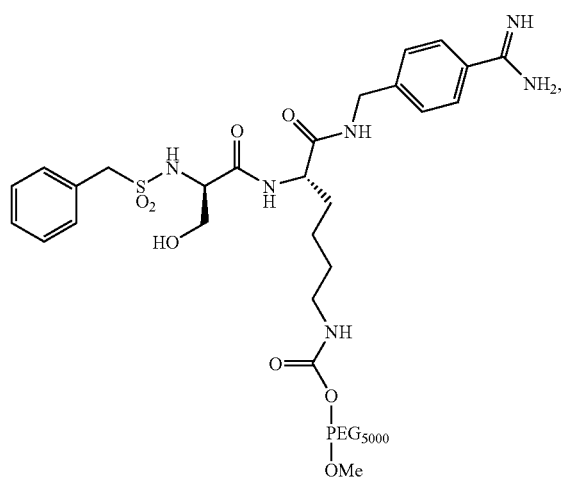

where PEG$_{5000}$ is a polyethylene glycol chain having an average molecular weight of 5000 Da, with it likewise being possible to use polyethylene glycol chains having an average molecular weight of 100-20000 Da;

or

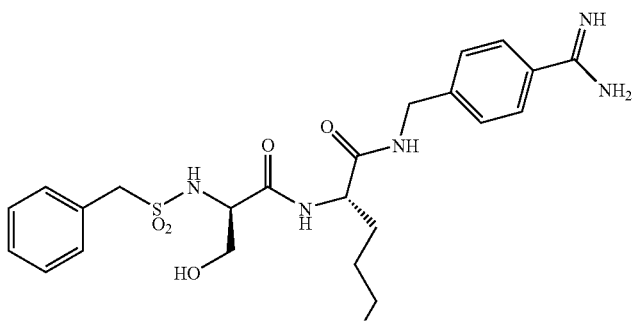

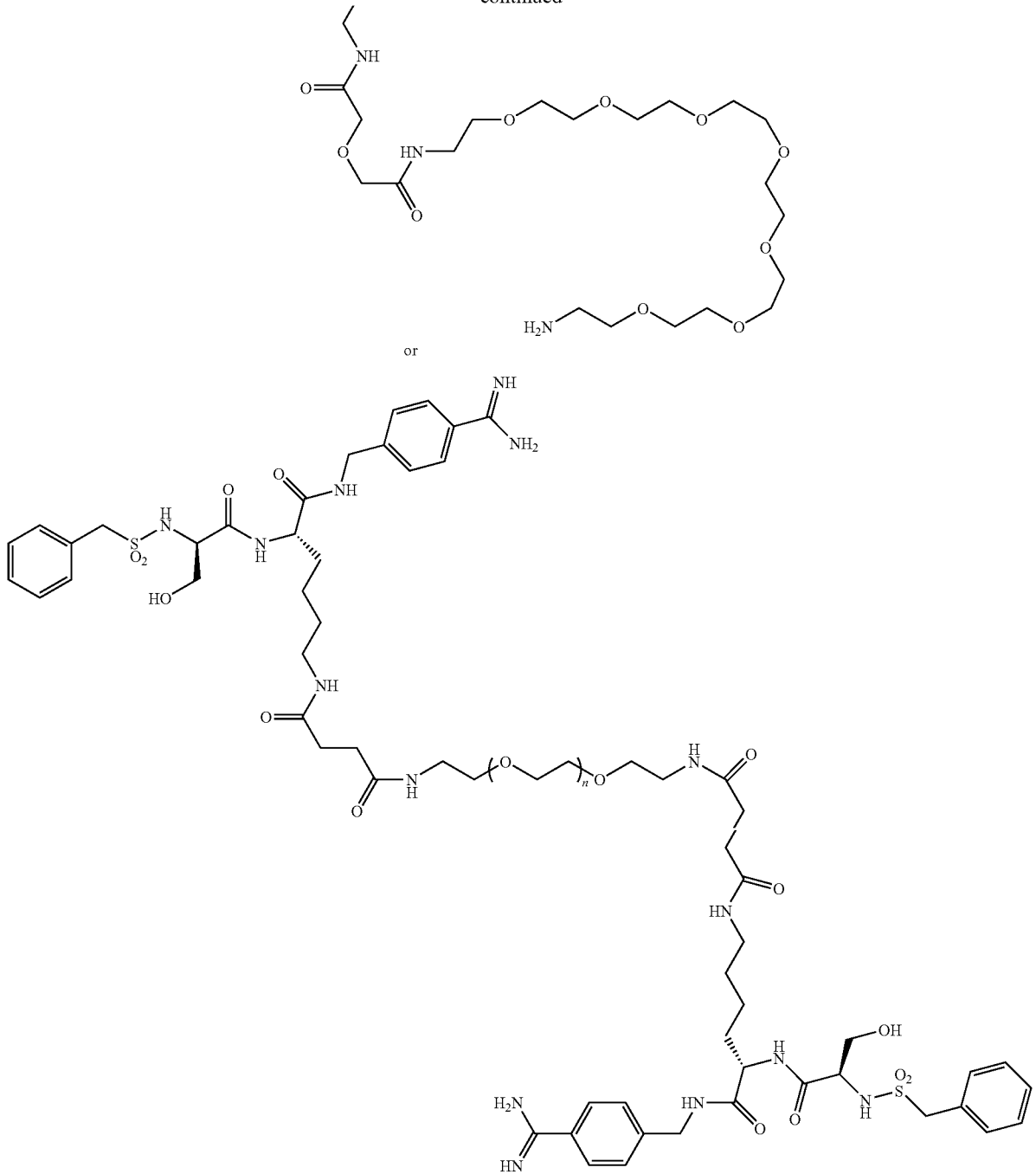

or in which n=2 to 250.

While inactivating urokinase more powerfully, the additionally charged 4-amidinobenzylamine derivatives are advantageously and surprisingly very slowly eliminated such that the compounds according to the invention constitute a novel group of highly active urokinase inhibitors.

Examples of these compounds are, in addition to those mentioned in the exemplary embodiments:

(3-pyridylmethyl)sulfonyl-dSer-Gly-4-amidinobenzylamide
(3-pyridylmethyl)sulfonyl-dSer-Ala-4-amidinobenzylamide
(3-pyridylmethyl)sulfonyl-dSer-Ser-4-amidinobenzylamide
(3-pyridylmethyl)sulfonyl-dSer-Pro-4-amidinobenzylamide
(4-pyridylmethyl)sulfonyl-dSer-Ala-4-amidinobenzylamide
(4-pyridylmethyl)sulfonyl-dSer-Ser-4-amidinobenzylamide
(4-pyridylmethyl)sulfonyl-dSer-Pro-4-amidinobenzylamide
(2-pyridylmethyl)sulfonyl-dSer-Gly-4-amidinobenzylamide
(2-pyridylmethyl)sulfonyl-dSer-Ala-4-amidinobenzylamide
(2-pyridylmethyl)sulfonyl-dSer-Ser-4-amidinobenzylamide
(2-pyridylmethyl)sulfonyl-dSer-Pro-4-amidinobenzylamide
((3-(trifluoromethyl)phenyl)methyl)sulfonyl-dSer-Gly-4-amidinobenzylamide ((3-(trifluoromethyl)phenyl)methyl)sulfonyl-dSer-Ala-4-amidinobenzylamide
((3-(trifluoromethyl)phenyl)methyl)sulfonyl-dSer-Ser-4-amidinobenzylamide
((3-(trifluoromethyl)phenyl)methyl)sulfonyl-dSer-Pro-4-amidinobenzylamide
((4-(trifluoromethyl)phenyl)methyl)sulfonyl-dSer-Gly-4-amidinobenzylamide
((4-(trifluoromethyl)phenyl)methyl)sulfonyl-dSer-Ala-4-amidinobenzylamide
((4-(trifluoromethyl)phenyl)methyl)sulfonyl-dSer-Ser-4-amidinobenzylamide
((4-(trifluoromethyl)phenyl)methyl)sulfonyl-dSer-Pro-4-amidinobenzylamide
2-Cl-benzylsulfonyl-dSer-Gly-4-amidinobenzylamide
2-Cl-benzylsulfonyl-dSer-Ala-4-amidinobenzylamide
2-Cl-benzylsulfonyl-dSer-Pro-4-amidinobenzylamide
2-Cl-benzylsulfonyl-dSer-Ser-4-amidinobenzylamide
3-Cl-benzylsulfonyl-dSer-Gly-4-amidinobenzylamide
3-Cl-benzylsulfonyl-dSer-Ala-4-amidinobenzylamide
3-Cl-benzylsulfonyl-dSer-Pro-4-amidinobenzylamide
3-Cl-benzylsulfonyl-dSer-Ser-4-amidinobenzylamide
4-Cl-benzylsulfonyl-dSer-Ala-4-amidinobenzylamide
4-Cl-benzylsulfonyl-dSer-Pro-4-amidinobenzylamide
4-Cl-benzylsulfonyl-dSer-Ser-4-amidinobenzylamide
2-methylbenzylsulfonyl-dSer-Gly-4-amidinobenzylamide
2-methylbenzylsulfonyl-dSer-Ala-4-amidinobenzylamide
2-methylbenzylsulfonyl-dSer-Pro-4-amidinobenzylamide
2-methylbenzylsulfonyl-dSer-Ser-4-amidinobenzylamide
3-methylbenzylsulfonyl-dSer-Gly-4-amidinobenzylamide
3-methylbenzylsulfonyl-dSer-Ala-4-amidinobenzylamide
3-methylbenzylsulfonyl-dSer-Pro-4-amidinobenzylamide
3-methylbenzylsulfonyl-dSer-Ser-4-amidinobenzylamide
4-methylbenzylsulfonyl-dSer-Ala-4-amidinobenzylamide
4-methylbenzylsulfonyl-dSer-Pro-4-amidinobenzylamide
4-methylbenzylsulfonyl-dSer-Ser-4-amidinobenzylamide Acylated 4-amidinobenzylamine which possesses, as $P_1$ ($P_2$) amino acid, a natural or artificial, unsubstituted or substituted basic amino acid in the L configuration, particularly preferably arginine or lysine, forms, when D-serine is bonded as the $P_2$ (P3) residue, and when the compound possesses an N-terminal protecting group $R_5$ composed of an aryl- or aralkyl-sulfonyl radical, is a particularly preferred inhibitor of urokinase which possesses high affinity and which is likewise particularly slowly eliminated.

While powerfully inactivating urokinase, the additionally charged 4-amidinobenzylamine derivatives are advantageously and surprisingly very slowly eliminated, such that the compounds according to the invention constitute a novel group of highly active urokinase inhibitors.

Examples of these compounds, in addition to those already mentioned, are:
benzylsulfonyl-dSer-homoLys-4-amidinobenzylamide
benzylsulfonyl-dSer-norArg-4-amidinobenzylamide
benzylsulfonyl-dSer-homoArg-4-amidinobenzylamide
benzylsulfonyl-dSer-Orn-4-amidinobenzylamide
benzylsulfonyl-dSer-Orn(2-imidazolinyl)-4-amidinobenzylamide
benzylsulfonyl-dSer-His-4-amidinobenzylamide
benzylsulfonyl-dSer-Dab-4-amidinobenzylamide
N-(4-amidinobenzyl)benzylsulfonyl-dSer-4-[(2-amino)pyrimidinyl]butyramide
benzylsulfonyl-dSer-Dap-4-amidinobenzylamide
benzylsulfonyl-dSer-Ala[3-(2-pyrrolidinyl)]-4-amidinobenzylamide
benzylsulfonyl-dSer-Ala[3-pyrrolidinyl-(2-N-amidino)]-4-amidinobenzylamide
benzylsulfonyl-dSer-Ala[3-(N-piperazine-4-N-amidino]-4-amidinobenzylamide
benzylsulfonyl-dSer-Ala(4-Pip)-4-amidinobenzylamide
benzylsulfonyl-dSer-Ala[4-Pip(N-amidino)]-4-amidinobenzylamide
benzylsulfonyl-dSer-homoAla(4-Pip)-4-amidinobenzylamide
benzylsulfonyl-dSer-Ala[3-Pip(N-amidino)]-4-amidinobenzylamide
benzylsulfonyl-dSer-homoAla(3-Pip)-4-amidinobenzylamide
benzylsulfonyl-dSer-homoAla[4-Pip(N-amidino)]-4-amidinobenzylamide
benzylsulfonyl-dSer-Ala-(3-guanidino)-4-amidinobenzylamide
benzylsulfonyl-dSer-Phe(3-amidino)-4-amidinobenzylamide
benzylsulfonyl-dSer-Phe(4-amidino)-4-amidinobenzylamide
benzylsulfonyl-dSer-Phe(3-$NH_2$)-4-amidinobenzylamide
benzylsulfonyl-dSer-Phe(4-$NH_2$)-4-amidinobenzylamide
benzylsulfonyl-dSer-Phe(3-guanidino)-4-amidinobenzylamide
benzylsulfonyl-dSer-Phe(4-guanidino)-4-amidinobenzylamide
benzylsulfonyl-dSer-Phe[4-(2-imidazolinyl)]-4-amidinobenzylamide
benzylsulfonyl-dSer-Phe[3-$CH_2$-(guanidino)]-4-amidinobenzylamide
benzylsulfonyl-dSer-Phe[4-$CH_2$-(guanidino)]-4-amidinobenzylamide
benzylsulfonyl-dSer-homoPhe(3-amidino)-4-amidinobenzylamide
benzylsulfonyl-dSer-homoPhe(4-amidino)-4-amidinobenzylamide
benzylsulfonyl-dSer-hPhe(3-$NH_2$)-4-amidinobenzylamide
benzylsulfonyl-dSer-hPhe(4-$NH_2$)-4-amidinobenzylamide
benzylsulfonyl-dSer-hPhe(3-guanidino)-4-amidinobenzylamide
benzylsulfonyl-dSer-hPhe(4-guanidino)-4-amidinobenzylamide
benzylsulfonyl-dSer-cis-Cha(4-$NH_2$)-4-amidinobenzylamide
benzylsulfonyl-dSer-trans-Cha(4-$NH_2$)-4-amidinobenzylamide
benzylsulfonyl-dSer-cis-homoCha(4-$NH_2$)-4-amidinobenzylamide
benzylsulfonyl-dSer-trans-homoCha(4-$NH_2$)-4-amidinobenzylamide
benzylsulfonyl-dSer-trans-Cha(4-$CH_2NH_2$)-4-amidinobenzylamide
benzylsulfonyl-dSer-trans-homoCha(4-$CH_2NH_2$)-4-amidinobenzylamide The compounds are as a rule present as salts, preferably with mineral acids, preferably as hydrochlorides, or preferably as salts with suitable organic acids. Sulfates are also preferred salts of mineral acids. Examples of suitable organic acids are acetic acid, formic acid, methylsulfonic acid, succinic acid, malic acid or trifluoroacetic acid, with acetates being preferred salts of organic acids.

The compounds of the general formula I can in principle be prepared in a known manner, as described below, for example as follows:

Methods known to the skilled person (Judkins et al., Synth. Commun. 26, 4351 (1996)) are used to obtain Boc-protecting 4-acetyloxamidinobenzylamine from the commercially available 4-cyanobenzylamine (Showa Denka, Japan). After the Boc protecting group has been eliminated, standard coupling methods are used to couple on the other amino acids and the protecting group $R_5$, employing Boc as the N-terminal protecting group. The $P_2$ (P3) amino acid can also be coupled directly as an N-aryl- or N-aralkyl-sulfonyl-protected amino acid. The peptide analogs are constructed sequentially, beginning with the acetyloxamidinobenzylamine. Most of the intermediates crystallize well and can consequently be purified readily. At the last step, the inhibitors are preferably finally purified by means of preparative, reversed-phase HPLC.

The present invention also relates to a process for preparing a compound of the general formula I or II, which comprises sequentially coupling the appropriate amino acids to a 4-acetyloxamidinobenzylamine, with either the N-terminal amino acid already carrying the $R_5$ radical or this radical subsequently being bonded to the amino acid.

The invention also relates to a pharmaceutical which comprises an inhibitor according to the invention as well as additional pharmaceutically suitable auxiliary substances and/or additives. Suitable auxiliary substances and/or additives, which are used, for example, for stabilizing and/or preserving the pharmaceutical, are well known to the skilled person (e.g. Sucker H. et al., (1991) Pharmazeutische Technologie [Pharmaceutical Technology], $2^{nd}$ edition, Georg Thieme Verlag, Stuttgart). They include, for example, physiological sodium chloride solutions, Ringer dextrose, Ringer lactate, demineralized water, stabilizers, antioxidants, sequestering agents, antimicrobial compounds, proteinase inhibitors and/or inert gases.

The pharmaceutical could be used, for example, in a parenteral use form, in particular in an intraarterial, intravenous, intramuscular or subcutaneous form, in an enteral use form, in particular for oral or rectal use, or in a topical use form, in particular as a skin-treatment agent. Intravenous or subcutaneous uses are preferred.

In one embodiment of the invention, the pharmaceutical is, for example, employed in the form of a tablet, of a sugar-coated tablet, of a capsule, of a pellet, of a suppository, of a solution, in particular of an injection solution or infusion solution, of eye drops, nose drops and ear drops, of a juice, of a capsule, of an emulsion or suspension, of a globule, of a stylus, of an aerosol, of a powder, of a paste, of a cream or of an ointment.

The urokinase inhibitors according to the invention, or the abovementioned pharmaceuticals, are preferably used for the diagnosis, therapy or prophylaxis of a tumor, in particular for reducing the formation of tumor metastases, preferably in oral, subcutaneous, intravenous or transdermal form.

The invention will be clarified below, without restricting it, using 14 exemplary embodiments:

BRIEF DESCRIPTION OF THE DRAWING

FIG. 1 shows the elimination of benzylsulfonyl-D-Ser-Gly, as well as derivatives containing Ala or Glu in the P2 position, following i.v. administration and as determined by means of HPLC.

METHODS

Figure 1:
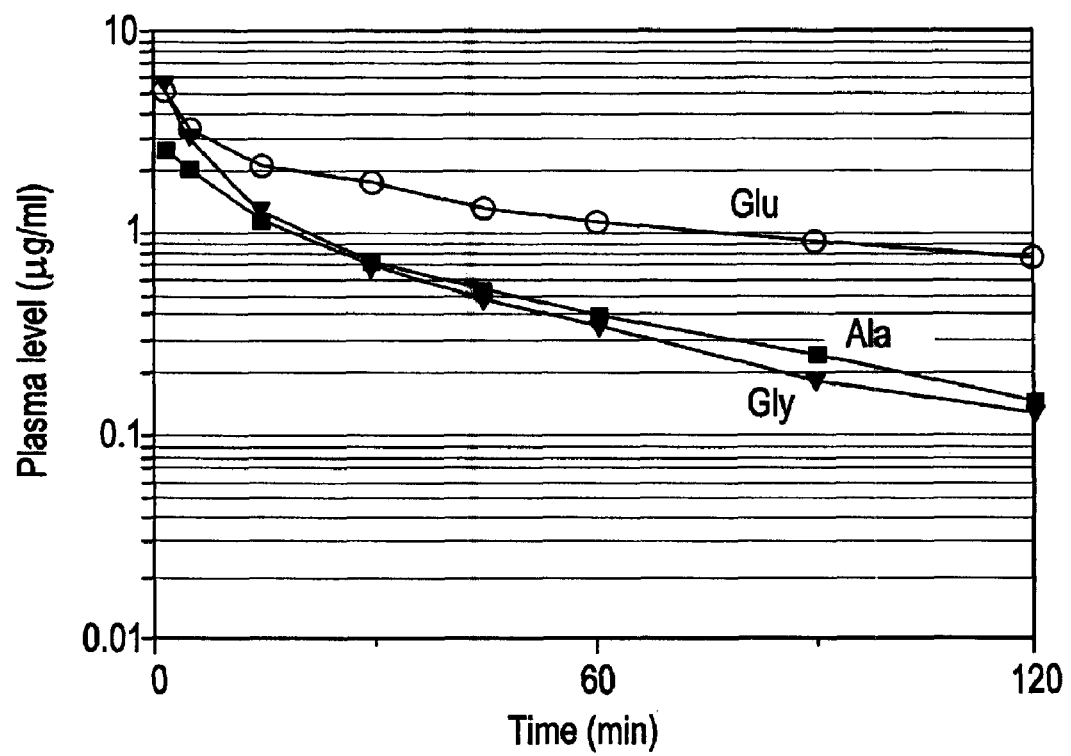
FIG. 1.

Analytical HPLC: Shimadzu LC-10A system, column: Vydac $C_{18}$, 5 μm (250×4 mm) solvent A: 0.1% TFA in water, B: 0.1% TFA in ACN, gradient: from 10% B to 60% B in 50 min, 1 ml/min flow rate, detection at 220 or 215 nm.

Preparative HPLC: Shimadzu LC-8A system, column: Knauer $C_{18}$, 5 μm (250×32 mm) solvent A: 0.1% TFA in water, B: 0.1% TFA in ACN, gradient: from 10% B to 55% B in 120 min, 10 ml/min flow rate, detection at 220 nm.

Mass spectroscopy: the mass spectra were measured on a Kratos Compact Probe (Manchester, England) using a time-of-flight measurement detector and α-cyanohydroxycinnamic acid as the matrix, or else on a Finnigan ESI-MS LCQ (Bremen, Germany).

EXAMPLE 1

Synthesizing benzylsulfonyl-D-Ser-Glu-4-amidinobenzylamide×TFA

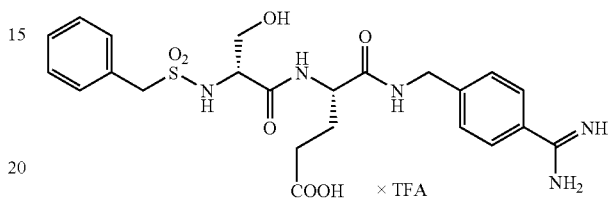

1a) Boc-4-cyanobenzylamide 20 g (0.151 mol) of 4-cyanobenzylamine were dissolved in 300 ml of $H_2O$, 150 ml of dioxane and 150 ml of 1 N NaOH. While cooling with ice, 37.5 ml of di-tert-butyl dicarbonate were added dropwise and the mixture was stirred at 0° C. for one hour and then at room temperature for a further 24 hrs. The dioxane was removed i.v. and the product was taken up in ethyl acetate and a 5% solution of $KHSO_4$. The ethyl acetate phase was washed 3 times with a 5% solution of $KHSO_4$ and 3 times with a saturated solution of NaCl, dried over $Na_2SO_4$ and evaporated i.v. (white crystals). HPLC: acetonitrile/$H_2O$, elution at 44.1% acetonitrile; yield: 30.48 g (0.131 mol), 87%.

1b) Boc-4-acetyloxamidinobenzylamide

In accordance with Judkins et al. (Synthetic Comm. 26, 4351-4367, 1996), 30.48 g (0.131 mol) of Boc-4-cyano-benzylamide, 13.65 (0.197 mol) of hydroxylamine×HCl and 34 ml (0.197 mol) of DIEA were dissolved in 300 ml of abs. ethanol. The mixture was boiled under reflux for 2 hrs and stirred overnight at room temperature. After that, the mixture was evaporated i.v. and the residue was dissolved in approx. 200 ml of acetic acid; 18.67 ml (0.197 mol) of acetic anhydride were then added to this solution. After 1 hr, the mixture was evaporated once again and the residue was dissolved in ethyl acetate; this solution was then washed, at 0° C., in each case 3 times with a 5% solution of $KHSO_4$ and a saturated solution of NaCl. After drying over $Na_2SO_4$ and concentrating i.v., a white powder accrued. HPLC: acetonitrile/$H_2O$, elution at 32.0% acetonitrile; yield: 31.3 g (0.102 mol) 78%.

1c) 4-Acetyloxamidinobenzylamine×HCl 5 mmol of Boc-4-acetyloxamidinobenzylamide are dissolved in 20 ml of 1 N HCl in glacial acetic acid and the mixture is left to stand at room temperature for 45 min. It is then extensively evaporated i.v., after which the product is precipitated with dry diethyl ether, filtered off on a sinter filter, washed once again with fresh ether and dried i.v. Because of the quantitative reaction, the product was used for the next step of the synthesis without any further purification.

1d) Boc-Glu(OBzl)-4-acetyloxamidinobenzylamide

Boc-Glu(OBzl)-OH (Orpegen, Heidelberg) was coupled to 4-acetyloxamidinobenzylamine×HCl in accordance with Frérot et al. (Tetrahedron 47, 259 ff., 1991). For this, 2.27 g (9.3 mmol) of 4-acetyloxamidinobenzylamine×HCl and 3.138 g (9.3 mmol) of Boc-Glu(OBzl)-OH were dissolved in approx. 25 ml of DMF. 4.84 g (9.3 mmol) of PyBOP and 3.878 ml (27.9 mmol) of TEA were added at 0° C. and the pH was adjusted to 9 using TEA. After the mixture had been stirred at room temperature for 1 hr, it was evaporated i.v. and the residue was taken up in ethyl acetate; this solution was then washed in each case 3 times with an acid solution, an alkaline solution and a neutral solution and then dried with $Na_2SO_4$ and evaporated i.v. Yield: 4.1 g (7.8 mmol) 84%.

1e) H-Glu(OBzl)-4-acetyloxamidinobenzylamide×HCl 4.1 g of Boc-Glu(Bzl)-4-acetyloxamidinobenzylamide were dissolved in 100 ml of 1 N HCl in glacial acetic acid and the solution was left to stand at room temperature for 45 min. It was then extensively evaporated i.v. and the residue was precipitated with dry diethyl ether; after that, the product was filtered off on a sinter filter and washed once again with fresh ether. After the product had been dried i.v., it was used without further purification for the synthesis in accordance with item 1g).

1f) Benzylsulfonyl-D-Ser(Bzl)-OH 229 mg (1.173 mmol) of H-D-Ser(Bzl)-OH and 408 µl (2.345 mmol) of DIEA were dissolved in 50 ml of 50% acetonitrile. 335 mg (1.76 mmol) of benzylsulfonyl chloride were then added and the mixture was stirred at room temperature for 12 hrs. It was evaporated i.v. and the residue was taken up in ethyl acetate; this solution was then washed in each case 3 times with an acid solution and a neutral solution. After drying over sodium sulfate, it was evaporated i.v. Yield: 289 mg (0.827 mmol) 71%.

1g) Benzylsulfonyl-D-Ser(Bzl)-Glu(OBzl)-4-acetylox-amidinobenzylamide 151 mg (0.433 mmol) of benzylsulfonyl-D-Ser(Bzl)-OH and 194 mg (0.433 mmol) of H-Glu(OBzl)-4-acetyloxamidinobenzylamide×HCl were dissolved in 5 ml of abs. DMF. While cooling with ice, 225 mg (0.433 mmol) of PyBOP and 230 µl (1.32 mmol) of DIEA were added. After 2 hrs, the mixture was evaporated i.v. and the residue was taken up in ethyl acetate; this solution was in each case washed 3 times with an acid solution, an alkaline solution and a neutral solution. After drying over sodium sulfate, it was evaporated i.v. and the residue was hydrogenated, without any further working-up, in accordance with item 1.8. Yield: 270 mg (0.364 mmol) 84%.

1h) Benzylsulfonyl-D-Ser-Glu-4-amidinobenzylamide×TFA 270 mg (0.364 mmol) of Bzls-D-Ser(Bzl)-Glu(OBzl)-4-acetyloxamidinobenzylamide were dissolved in 30 ml of 90% acetic acid. After that, 20 mg of 10% palladium on active charcoal were added and argon. The argon was replaced with a hydrogen atmosphere and the mixture was hydrogenated for 24 hrs while being stirred vigorously. The catalyst was filtered off and the filtrate was evaporated i.v.; the product was then purified by means of preparative reversed-phase HPLC (acetonitrile/$H_2O$, 0.1% trifluoroacetic acid, elution at 22.6% acetonitrile).

EXAMPLE 2

Inhibiting Urokinase with Selected 4-amidinobenzylamide Compounds

TABLE 1

| $R_5$ | Configuration $R_4$ | $R_4$ | $R_3$ | $X-R_2$ | $Y-R_1$ | $K_i$, µM |
|---|---|---|---|---|---|---|
| Bzl-$SO_2$ | D | $CH_2$—OH | H | $CH_2$ | $CH_2$ | 0.036 |
| Bzl-$SO_2$ | D | $CH_2$—OH | H | CH—$CH_3$ | $CH_2$ | 0.0077 |
| Bzl-$SO_2$ | D | $CH_2$—OH | H | CH—$CH_2$—COOH | $CH_2$ | 0.86 |
| Bzl-$SO_2$ | D | $CH_2$—OH | H | CH—($CH_2$—$)_2$—COOH | $CH_2$ | 0.16 |

Determining the Inhibitory Effect

In order to determine the inhibitory effect, 200 µl of Tris buffer (0.05 M, 0.154 M NaCl, 5% ethanol, pH 8.0; contains the inhibitor), 25 µl of substrate (Bzl-βAla-Gly-Arg-pNA in $H_2O$) and 50 µl of sc urokinase were incubated at 25° C. After 3 min, the reaction was terminated by adding 25 µl of acetic acid (50%) and the absorption at 405 nm was determined using a Microplate Reader (Dynatech MR 5000). The $K_i$ values were determined by linear regression in accordance with Dixon (Biochem. J. 55, 170-171, 1953) using a computer program. The $K_i$ values are the means of at least three determinations.

EXAMPLE 3

Elimination of benzylsulfonyl-D-Ser-Gly-4-amidinobenzylamide Derivatives Containing Ala or Glu in the P2 Position Following Their i.v. Administration, at the Rate of 1 mg/kg of Body Weight, to Rats Animal Experiments Female Wistar rats (240-300 g body weight) were anesthetized (ethylurethane, 2.5 g/ml in NaCl, 0.5 ml/100 g rat), after which the A. carotis located in the neck was exposed. A catheter inserted into this vessel enabled blood to be removed at specified times. The volume administered was 0.5 ml, while 0.9% NaCl was used as the administration solution. 500 µl blood samples (treated in a ratio of 19+1 with 1.04 M sodium citrate) were withdrawn at the following times: 2, 5, 15, 30, 45, 60, 90, 120, 150, 180, 210, 240 and 270 min. The resultant loss of blood was offset, immediately after removal of the sample, with 500 µl of 0.9% NaCl solution. Citrate plasma was obtained by centrifuging the blood at 1200×g for 10 min. The concentrations of the active compounds in the plasma were determined by means of HPLC (FIG. 1).

EXAMPLE 4

3-(HOOC)Benzylsulfonyl-dSer-Gly-4-amidinobenzylamide×TFA

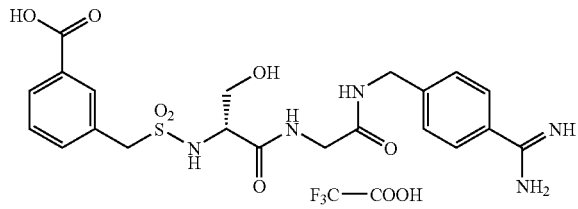

4a) 3-(COOMe)-Benzylsulfonic acid, Sodium Salt 5 g (21.1 mmol) of methyl 3-bromomethyl)benzoate (Lancaster) were suspended in 35 ml of water and, after 2.94 g (23.3 mmol) of $Na_2SO_3$ had been added, the whole was boiled under reflux for 8 h. The mixture was filtered in the hot and the water was evaporated off in vacuo until crystallization began. The mixture was stored overnight in a refrigerator and, after that, the crystals were filtered off with suction and recrystallized once again from water. The crystals were filtered off with suction and dried in vacuo.

Yield: 3.9 g (15.46 mmol) HPLC: 22.3% B 4b) 3-(COOMe)-Benzylsulfonyl chloride 2.5 g (9.91 mmol) of 3-(COOMe)-benzylsulfonic acid, sodium salt, were moistened with approx. 10 ml of phosphoryl chloride, after which 2.27 g (10.9 mmol) of $PCl_5$ were added and the whole was stirred in an icebath for 15 minutes. After that, the mixture was heated at 80° C. for 4 h. It was then poured onto ice and the whole was stirred vigorously for 30 min, after which the product separated out on the ice in the form of white crystals. After the ice had partially thawed, the mixture was filtered through a sintered filter and the product/ice mixture which remained was washed several times with water. The crystals which remained were dried in vacuo.

Yield: 1.6 g (6.43 mmol) 65% (white crystals)

4c) 3-(COOMe)-Benzylsulfonyl-dSer(tBu)-OH 0.75 g (4.65 mmol) of H-dSer(tBu)-OH (Bachem) was suspended in 60 ml of dry DCM, after which 1.23 ml (9.765 mmol) of trimethylsilyl chloride and 1.76 ml (9.765 ml) of DIEA were added. The mixture was boiled under reflux for 1.0 h and, after that, cooled in an icebath. 1.27 g (5.12 mmol) of 3-(COOMe)-benzylsulfonyl chloride and 1.04 ml (6 mmol) of DIEA were then added, in several portions, within the space of 30 min. The mixture was stirred for a further 15 min while cooling with ice and, after that, stirred at room temperature for 3 h. The solvent was removed in vacuo and the residue was dissolved in water (brought to pH 8.5-9 with 1 N NaOH) and extracted 2× with ether. The aqueous phase was acidified with a 5% solution of $KHSO_4$ and extracted 3× with ethyl acetate. The combined ethyl acetate phase was washed in each case 3× with a 5% solution of $KHSO_4$ and a saturated solution of NaCl and then dried with $Na_2SO_4$. After that, the solvent was removed in vacuo.

Yield: 1.3 g (3.48 mmol of solid), HPLC: 51% B

4d) H-Gly-4-acetyloxamidinobenzylamide×HCl 30 ml of 1 N HCl in glacial acetic acid were added to 2 g (5.49 mmol) of Boc-Gly-4-acetyloxamidinobenzylamide (prepared as described in WO 01/96286 A2). The mixture was shaken occasionally. After 45 min, the solvent was evaporated off to some degree and the product was precipitated by adding diethyl ether; after that, it was filtered off with suction on a frit, washed with ether and dried in vacuo.

Yield: 1.55 g (5.15 mmol), white solid 4e) 3-(COOMe)-Benzylsulfonyl-dSer(tBu)-Gly-4-acetylox-amidinobenzylamide 1 g (2.68 mmol) of 3-(COOMe)-benzylsulfonyl-dSer(tBu)-OH and 0.84 g (2.8 mmol) of H-Gly-4-acetyloxamidinobenzylamide×HCl were dissolved, while stirring and cooling with ice, in 15 ml of DMF, after which 1.39 g (2.68 mmol) of PyBop and 1.26 ml (7.236 mmol) of DIEA were added. After 30 min, the icebath was removed and the mixture was stirred at room temperature for a further 4 h. The DMF was evaporated off in vacuo and the residue which remained was dissolved in ethyl acetate; this solution was then washed, in each case 3×, with 5% $KHSO_4$, NaCl-saturated water, a saturated solution of $NaHCO_3$ and, once again, with NaCl-saturated water. The ethyl acetate phase was dried with $Na_2SO_4$, after which the solvent was removed in vacuo. The crude product was used for the next step of the synthesis without any further purification.

Yield: 1.35 g (2.18 mmol) of oil, HPLC: 47.89% B 4f) 3-(COOMe)-Benzylsulfonyl-dSer(tBu)-Gly-4-amidino-benzylamide×Acetate 1 g (1.61 mmol) of 3-(COOMe)-benzylsulfonyl-dSer(tBu)-Gly-4-acetyloxamidinobenzylamide was dissolved in 64 ml of 90% acetic acid, after which 150 mg of catalyst (10% Pd on active charcoal) were added and the mixture was hydrogenated overnight with hydrogen. The catalyst was filtered off and the solvent was evaporated in vacuo. Toluene was added to the residue which remained and, after that, the solvent was once again removed in vacuo. This procedure was repeated once again. The residue which remained was used directly for the next reaction step.

Yield: 0.9 g (1.44 mmol) of solid, HPLC: 39.75% B

Approx. 50 mg of the crude product were purified by means of preparative reversed-phase HPLC, and lyophilized.

MS: calculated, 561.2 (monoisotopic). found, 562.9 $[M+H]^+$ 4g) 3-(COOH)-Benzylsulfonyl-dSer(tBu)-Gly-4-amidinobenzylamide×TFA 750 mg (1.2 mmol) of 3-(COOMe)-benzylsulfonyl-dSer(tBu)-Gly-4-amidinobenzylamide×acetate were dissolved in 20 ml of methanol and 10 ml of water and 4 ml of 1 N LiOH were added. The mixture was stirred overnight, being neutralized (pH 6-7) with 5% $KHSO_4$ after approx. 15 h; the solvent was then removed in vacuo. The crude product was purified by means of preparative reversed-phase HPLC, and lyophilized.

HPLC: 34.16% B (white solid)

4h) 3-(COOH)-Benzylsulfonyl-dSer-Gly-4-amidinobenzylamide 0.5 ml of water and 4.5 ml of trifluoroacetic acid were added to 100 mg (0.151 mmol) of 3-(COOH)-benzylsulfonyl-dSer(tBu)-Gly-4-amidinobenzylamide. The mixture was left at room temperature for 60 min and, after that, the solvent was evaporated in vacuo. The residue was dissolved in water and then lyophilized.

Yield: 91 mg (white solid) HPLC: 23.47% B

EXAMPLE 5

Benzylsulfonyl-dSer-Ser-4-amidinobenzylamide× TFA

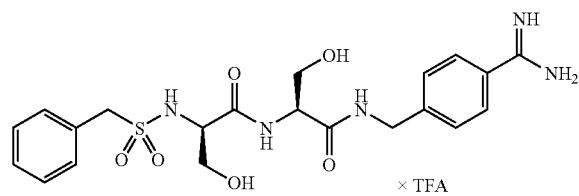

5a) Boc-Ser(Bzl)-4-Acetyloxamidinobenzylamide 4.847 g (16.41 mmol) of Boc-Ser(Bzl)-OH were dissolved in 50 ml of THF, after which 1.805 ml (16.41 mmol) of NMM and 2.133 ml of IBCC were added at −15° C. The mixture was stirred at −15° C. for 10 min, after which 4 g (16.41 mmol) of 4-(acetyloxamidino)benzylamine×HCl (prepared as described in WO 01/96286 A2) and, once again, 1.805 ml (16.41 mmol) of NMM were added. The mixture was stirred for a further hour at −15° C. and then overnight at room temperature. The solvent was removed in vacuo and the mixture was taken up in ethyl acetate; this solution was then washed, in each case 3×, with 5% $KHSO_4$, NaCl-saturated water, a saturated solution of $NaHCO_3$ and, once again, with NaCl-saturated water, after which it was dried with $Na_2SO_4$. The solvent was removed in vacuo and the product was crystallized from ethyl acetate.

Yield: 5.8 g (11.98 mmol) of white crystals, HPLC: 50.78% B

5b) H-Ser(Bzl)-4-Acetyloxamidinobenzylamide×HCl 30 ml of 1 N HCl in glacial acetic acid were added to 2 g (4.12 mmol) of Boc-Ser(Bzl)-4-acetyloxamidinobenzylamide. After 45 min of standing at room temperature, the solvent was partly evaporated off and the product was precipitated by adding diethyl ether; it was then filtered off with suction and washed once again with diethyl ether. The product was dried in vacuo.

Yield: 1.6 g (3.8 mmol) of white solid, HPLC: 28.51% B

5c) Bzls-dSer(tBu)-Ser(Bzl)-4-Acetyloxamidinobenzylamide 0.75 g (2.376 mmol) of Bzls-dSer(tBu)-OH and 1 g (2.376 mmol) of H-Ser(Bzl)-4-acetyloxamidinobenzylamide×HCl were dissolved in 20 ml of DMF, after which 1.236 g (2.376 mmol) of PyBop and 1.033 ml (5.94 mmol) of DIEA were added at 0° C. The mixture was stirred at 0° C. for 30 min and at room temperature for a further 4 h. The solvent was removed in vacuo and the residue was taken up in ethyl acetate; this solution was then washed, in each case 3×, with 5% $KHSO_4$, NaCl-saturated water, a saturated solution of $NaHCO_3$ and, once again, with NaCl-saturated water, and then dried with $Na_2SO_4$. The solvent was removed in vacuo. There then remained an oily crude product, which was used directly for the next step of the synthesis.

Yield: 1.15 g (1.69 mmol) of oil, HPLC: 60.48% B

5d) Bzls-dSer(tBu)-Ser(Bzl)-4-Amidinobenzylamide×Acetate 1 g (1.467 mmol) of Bzls-dSer(tBu)-Ser(Bzl)-4-acetyloxamidinobenzylamide was dissolved in 50 ml of 90% acetic acid, after which 150 mg of catalyst (10% Pd/C) were added. The mixture was hydrogenated with hydrogen for 6 h at room temperature and under standard pressure. The catalyst was then filtered off and the solvent was evaporated off in vacuo; toluene was added to the residue. The solvent was removed in vacuo and the procedure was repeated a further 2×. The residue which remained was dried in vacuo and used without any further purification for the next step in the synthesis.

Yield: 0.9 g (1.316 mmol) of oil, HPLC: 49.91% B.

5e) Bzls-dSer-Ser-4-Amidinobenzylamide×TFA 5 ml of TFA were added, while cooling with ice, to 0.2 g of Bzls-dSer(tBu)-Ser.(Bzl)-4-amidinobenzylamide×acetate crude product. After 10 min, 500 µl of trifluoromethanesulfonic acid were added. After a further 5 min, the icebath was removed and the mixture was left to stand at room temperature for 20 min. The product was precipitated by adding diethyl ether and centrifuged off. Diethyl ether was added once again to the precipitate, with this mixture being shaken and centrifuged once again. The precipitate was purified by means of preparative reversed-phase HPLC.

Yield: 75 mg, HPLC: 24.64% B

MS: calculated, 477.17 (monoisotopic), found, 478.6 [M+H]⁺.

EXAMPLE 6

4-(Aminomethyl)benzylsulfonyl-dSer-Gly-4-amidinobenzylamide×2 TFA

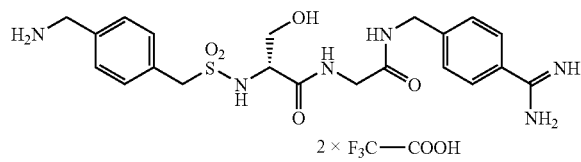

6a) 4-Cyanobenzylsulfonic acid, Sodium Salt 30 g (153 mmol) of 4-cyanobenzyl bromide (Aldrich) were suspended in 150 ml of water and, after 21.2 g (168.3 mmol) of $Na_2SO_3$ had been added, boiled under reflux for 8 h. The mixture was filtered in the hot and some of the water was evaporated off in vacuo. The mixture was stored in a refrigerator overnight to allow crystallization to occur; after that, the crystals were filtered off with suction and recrystallized once again from water. The crystals were filtered off with suction and dried in vacuo.

Yield: 17.1 g (78 mmol), HPLC: 18.24% B

6b) 4-Cyanobenzylsulfonyl chloride 5 g (22.83 mmol) of 4-cyanobenzylsulfonic acid, sodium salt, were moistened with approx. 20 ml of phosphoryl chloride after which 5.2 g (25.11 mmol) of $PCl_5$ were added and the mixture was stirred for 15 min while being cooled with ice. The mixture was then heated at 80° C. for 4 h. After that, the mixture was poured onto ice and this fresh mixture was stirred vigorously for 30 min; the product then separated out on the ice as a white solid. After the ice had partially thawed, the mixture was filtered through a frit and the product/ice mixture which remained was washed several times with water. The crystals which remained were dried in vacuo and used directly for the next step in the synthesis.

Yield: 3.4 g (15.76 mmol)

6c) 4-Cyanobenzylsulfonyl-dSer(tBu)-OH 1 g (6.2 mmol) of H-dSer(tbU)-OH (Bachem) was suspended in 50 ml of dry DCM, after which 1.65 ml (13 mmol) of trimethylsilyl chloride and 2.26 ml (13 mmol) of DIEA were added. The mixture was boiled under reflux for 1 h and then cooled in an icebath. 1.47 g (6.82 mmol) of 4-cyanobenzylsulfonyl chloride and 1.19 ml (6.82 mmol) of DIEA were then added within the space of 30 min. The mixture was stirred for a further 15 min while being cooled with ice and, after that, for a further 3 h at room temperature. The solvent was removed in vacuo and the residue was dissolved in water (brought to pH 8.5-9 with 1 N NaOH); this solution was extracted 2× with ether. After that, the aqueous phase was acidified with a 5% solution of $KHSO_4$ and extracted 3× with ethyl acetate. The combined ethyl acetate phase was washed in each case 3× with a 5% solution of $KHSO_4$ and a saturated solution of NaCl, and dried with $Na_2SO_4$. The solvent was removed in vacuo.

Yield: 1.4 g (4.11 mmol of solid), HPLC: 48.89% B

6d) 4-Cyanobenzylsulfonyl-dSer(tBu)-Gly-4-acetyloxamidinobenzylamide 1 g (2.94 mmol) of 4-cyanobenzylsulfonyl-dSer(tBu)-OH and 0.884 g (2.94 mmol) of H-Gly-4-acetyloxamidinobenzylamide×HCl (see Example 1d) were dissolved, while stirring and cooling with ice, in 15 ml of DMF, after which 1.53 g (2.94 mmol) of PyBop and 1.38 ml (7.94 mmol) of DIEA were added. After 30 min, the icebath was removed and the mixture was stirred at room temperature for a further 4 h. The DMF was evaporated off in vacuo and the residue which remained was dissolved in ethyl acetate; this solution was then washed, in each case 3×, with 5% $KHSO_4$, NaCl-saturated water, a saturated solution of $NaHCO_3$ and, once again, with NaCl-saturated water, after which it was dried using $Na_2SO_4$. The solvent was removed in vacuo. The crude product was used for the next step in the synthesis without any further purification.

Yield: 1.4 g (2.386 mmol) of oil, HPLC: 46.05% B

6e) 4-Cyanobenzylsulfonyl-dSer(tBu)-Gly-4-amidinobenzylamide×Acetate 1 g (1.7 mmol) of 4-cyanobenzylsulfonyl-dSer(tBu)-Gly-4-acetyloxamidinobenzylamide was dissolved in 70 ml of 90% acetic acid, after which 150 mg of catalyst (10% Pd on active charcoal) were added and the mixture was hydrogenated with hydrogen for 5 h. The catalyst was filtered off and the solvent was evaporated. The residue which remained was treated with toluene, after which the solvent was removed in vacuo. This procedure was repeated once again. The residue which remained was used directly for the next step in the reaction.

Yield: 0.85 g (1.44 mmol as the acetate salt) of solid HPLC: 37.55% B

Approx. 60 mg of this crude product were purified by means of preparative HPLC.

MS: calculated, 528.2 (monoisotopic). found, 530.1 $[M+H]^+$.

6f) 4-Aminomethylbenzylsulfonyl-dSer(tBu)-Gly-4-amidinobenzylamide×2 TFA 200 mg of 4-cyanobenzylsulfonyl-dSer(tBu)-Gly-4-amidinobenzylamide×acetate crude product were dissolved in 50 ml of 90% acetic acid and 5 ml of 1 N HCl, after which 40 mg of catalyst (10% Pd on active charcoal) were added and the mixture was hydrogenated with hydrogen overnight at 40° C. The catalyst was filtered off and the solvent was evaporated in vacuo. The residue which remained was purified by means of preparative reversed-phase HPLC.

Yield: 75 mg (as 2× TFA salt) of solid HPLC: 26.05% B

MS: calculated, 532.25 (monoisotopic). found, 533.7 $[M+H]^+$.

6g) 4-Aminomethylbenzylsulfonyl-dSer-Gly-4-amidinobenzylamide×2 TFA 0.2 ml of water and 1.8 ml of TFA were added to 25 mg (0.033 mmol) of 4-aminomethylbenzylsulfonyl-dSer(tBu)-Gly-4 -amidiniobenzylamide×2 TFA. The mixture was left at room temperature for 60 min and the solvent was evaporated off in vacuo. The residue was treated with approx. 10 ml of water and lyophilized.

Yield: 20 mg (of a faintly yellowish solid) HPLC: 15.4% B

MS: calculated, 476.18 (monoisotopic). found, 477.5 $[M+H]^+$.

TABLE 2

Inhibition constants ($K_i$ in μM) and elimination (β phase) half-lives ($t_{1/2}$ in h) in rats, following intravenous administration at a rate of 1 mg/kg, for inhibitors possessing the general structure. The inhibition constants ($K_i$ and $t_{1/2}$) for uPA were determined as described in Stürzebecher et al., (1997) J Med Chem Vol. 40, 3091-3099, while those for plasmin, trypsin and thrombin were determined in analogy therewith.

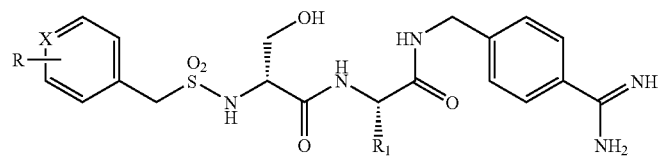

| | | | $K_i$ (μM) | | | | |
|---|---|---|---|---|---|---|---|
| R | X | R1 | uPA | plasmin | trypsin | thrombin | $t_{1/2}$ (h) |
| H | CH | H | 0.036 | 11 | 0.15 | 13 | 0.29 |
| 3-COOMe | CH | H | 0.12 | 28 | 0.29 | 42 | n.d. |

TABLE 2-continued

Inhibition constants ($K_i$ in µM) and elimination (β phase) half-lives ($t_{1/2}$ in h) in rats, following intravenous administration at a rate of 1 mg/kg, for inhibitors possessing the general structure. The inhibition constants ($K_i$ and $t_{1/2}$) for uPA were determined as described in Stürzebecher et al., (1997) J Med Chem Vol. 40, 3091-3099, while those for plasmin, trypsin and thrombin were determined in analogy therewith.

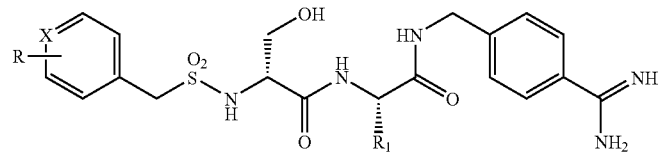

| R | X | R1 | uPA | plasmin | trypsin | thrombin | $t_{1/2}$ (h) |
|---|---|---|---|---|---|---|---|
| | | | | $K_i$ (µM) | | | |
| 3-COOH | CH | H | 0.16 | 59 | 0.72 | 150 | 1.3 |
| 4-COOMe | CH | H | 0.62 | 17 | 0.18 | 9.4 | n.d. |
| 4-COOH | CH | H | 0.15 | 35 | 0.48 | 170 | 2.0 |
| 2-COOMe | CH | H | 0.083 | 38 | 0.40 | 4.0 | n.d. |
| 2-COOH | CH | H | 0.37 | 220 | 2.4 | 56 | n.d. |
| 4-COOH | CH | $CH_3$ | 0.038 | 3.0 | 0.013 | 2.3 | 0.66 |
| 3-COOH | CH | $CH_3$ | 0.030 | 4.7 | 0.021 | 8.3 | 0.42 |
| 4-CN | CH | CH | 0.089 | 27 | 0.34 | 8.5 | n.d. |
| 4-($NH_2$—$CH_2$) | CH | H | 0.12 | 7.4 | 0.28 | 8.0 | n.d. |
| H | CH | $CH_2$—OH | 0.025 | 0.75 | 0.022 | 14 | 0.50 |
| H | CH | $CH_2$—O(Bzl) | 0.028 | 0.27 | 0.0068 | 0.48 | n.d. |
| H | CH | $CH_2$—$NH_2$ | 0.036 | 0.81 | 0.021 | 0.78 | 0.40 |
| H | CH | $CH(OH)CH_3$ | 0.11 | 1.4 | 0.03 | 4.0 | n.d. |
| H | CH | $CH(OBzl)CH_3$ | 0.061 | 1.1 | 0.011 | 0.10 | n.d. |
| 3-COOH | CH | $CH_2$—OH | 0.075 | 4.2 | 0.058 | 200 | 0.43 |
| 4-COOH | CH | $CH_2$—OH | 0.23 | 6.2 | 0.10 | 120 | 0.43 |
| 4-COOMe | CH | $CH_2$—OH | 0.23 | 0.96 | 0.020 | 4.2 | n.d. |
| 4-Cl | CH | H | 0.032 | 32 | 0.35 | 7.9 | n.d. |
| 4-Me | CH | H | 0.058 | 18 | 0.21 | 8.0 | n.d. |
| 4-F | CH | H | 0.031 | 20 | 0.11 | 7.9 | n.d. |
| 3,4-di-Cl | CH | H | 0.11 | 32 | 0.60 | 8.3 | n.d. |
| H | N | H | 0.10 | 37 | 0.41 | 1.6 | n.d. |

*n.d. = not determined

EXAMPLE 7

Benzylsulfonyl-dSer-Lys-4-amidinobenzylamide×2 TFA

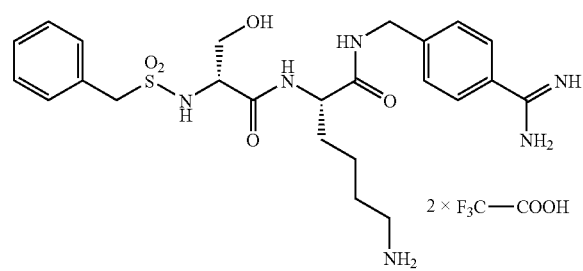

7a) Boc-Lys(Tfa)-4-Acetyloxamidinobenzylamide 5 g (14.61 mmol) of Boc-Lys(Tfa)-OH were dissolved in 100 ml of THF after which 1.767 ml (16.10 mmol) of NMM and 1.899 ml (14.61 mmol) of IBCC were added at −15° C. The mixture was stirred at −15° C. for 10 min, after which 3.74 g (15.33 mmol) of 4-(acetyloxamidino)benzylamine×HCl (prepared as described in WO 01/96286 A1) and, once again, 1.767 ml (16.10 mmol) of NMM were added. The mixture was stirred at −15° C. for a further hour and then at room temperature overnight. The solvent was removed in vacuo and the residue was taken up in ethyl acetate; this solution was washed, in each case 3×, with 5% $KHSO_4$, NaCl-saturated water, a saturated solution of $NaHCO_3$ and, once again, with NaCl-saturated water, and dried with $Na_2SO_4$. The solvent was removed in vacuo and the product was crystallized from ethyl acetate.

Yield: 6.82 g (12.83 mmol) of white crystals, HPLC: 43.87% B

7b)

H-Lys(Tfa)-4-Acetyloxamidinobenzylamide×HCl 5 g (9.41 mmol) of Boc-Lys(Tfa)-4-acetyloxamidinobenzylamide were solubilized in a little glacial acetic acid, after which 100 ml of 1 N HCl in glacial acetic acid were added. After the mixture had stood at room temperature for 45 min, the solvent was partially evaporated off and the product was precipitated by adding diethyl ether, filtered off with suction and washed once again with diethyl ether. The product was dried in vacuo.

Yield: 4.65 g (10.78 mmol) of a white solid, HPLC: 25.52% B

7c) Bzls-dSer(tBu)-Lys(Tfa)-4-Acetyloxamidinobenzylamide 1.93 g (6.107 mmol) of Bzls-dSer(tBu)-OH and 3 g (6.412 mmol) of H-Lys(Tfa)-4-axcetyloxamidinobenzylamide×HCl were dissolved in 30 ml of acetonitrile, after which 3.337 g (6.412 mmol) of PyBop and 3.187 ml (18.32 mmol) of DIEA were added at 0° C. The mixture was stirred at 0° C. for 30 min and then at room temperature for a further 4 h. The solvent was removed in vacuo and the residue was taken up in ethyl acetate; this solution was washed, in each case 3×, with 5% $KHSO_4$, NaCl-saturated water, a saturated solution of $NaHCO_3$ and, once again, with NaCl-saturated water, and then dried with $Na_2SO_4$. The solvent was removed in vacuo. There then remained a slightly yellow, amorphous crude product, which was used directly for the next step in the synthesis without any further purification.

Yield: 5.88 g (crude product), HPLC: 52.93% B

7d) Bzls-dSer(tBu)-Lys(Tfa)-4-Amidinobenzylamide×Acetate 5.88 g of Bzls-dSer(tBu)-Lys(Tfa)-4-(acetyloxamidino)-benzylamide (crude product) were dissolved in 150 ml of 90% acetic acid and 500 mg of catalyst (10% Pd/C) were added to this solution. The mixture was hydrogenated with hydrogen for 6 h at room temperature and under standard pressure. The catalyst was then filtered off and the solvent was partially evaporated; the product was then precipitated by adding diethyl ether, filtered off with suction and washed once again with diethyl ether. The white, crystalline precipitate was dried in vacuo.

Yield: 4.36 g (5.962 mmol), HPLC: 43.50% B.

7e) Bzls-dSer-Lys-4-Amidinobenzylamide×2 TFA 5 ml of a 1M aqueous solution of piperidine were added to 0.2 g of Bzls-dSer(tBu)-Lys(Tfa)-4-amidinobenzylamide× acetate crude product, while cooling with ice, and the mixture was stirred for 3 h. 45 ml of TFA were then added. After the mixture had been stirred at room temperature for 1 h, the solvent was evaporated off in vacuo and toluene was added to the residue; the solvent was then removed in vacuo once again. This procedure was repeated a further 2×. The residue which remained was dried in vacuo and, without any further purification, was purified by means of preparative reversed-phase HPLC.

Yield: 65 mg, HPLC: 21.19% B

MS: calculated, 574.26 (monoisotopic). found, 574.3 $[M+H]^+$.

EXAMPLE 8

Benzylsulfonyl-dSer-Arg-4-amidinobenzylamide×2 TFA

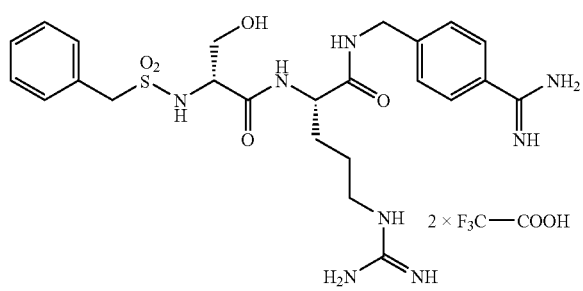

8a) Boc-Arg(Boc)$_2$-4-Acetyloxamidinobenzylamide 0.5 g (1.05 mmol) of Boc-Arg(Boc)$_2$-OH were dissolved in 25 ml of THF, after which 122 µl (1.11 mmol) of NMM and 137 µl (1.05 mmol) of IBCC were added at −15° C. The mixture was stirred at −15° C. for 10 min, after which 0.274 g (1.11 mmol) of 4-(acetyloxamidino)benzylamine×HCl (prepared as described in WO 01/96286 A2) and, once again, 122 µl (1.11 mmol) of NMM were added. The mixture was stirred for a further hour at −15° C. and overnight at room temperature. The solvent was removed in vacuo and the residue was taken up in ethyl acetate; this solution was then washed, in each case 3×, with 5% $KHSO_4$, NaCl-saturated water, a saturated solution of $NaHCO_3$ and, once again, with NaCl-saturated water, and dried with $Na_2SO_4$. The solvent was removed in vacuo, with the product accruing as a white, amorphous substance.

Yield: 0.654 g (0.985 mmol), HPLC: 48.89% B

8b) H-Arg-4-Acetyloxamidinobenzylamide×HCl 0.65 g (0.979 mmol) of Boc-Arg(Boc)$_2$-4-acetyloxamidinobenzylamide was solubilized in a little glacial acetic acid and 100 ml of 1 N HCl in glacial acetic acid were then added. After the mixture had stood at room temperature for 45 min, the solvent was partially evaporated off and the product was precipitated by adding diethyl ether, filtered off with suction and washed once again with diethyl ether. The product was dried in vacuo.

Yield: 0.459 g (0.971 mmol) of white solid, HPLC: 17.01% B

8c) Bzls-dSer(tBu)-Arg-4-(Acetyloxamidino)benzylamide 0.2 g (0.634 mmol) of Bzls-dSer(tBu)-OH and 0.3 g (0.634 mmol) of H-Arg-4-acetyloxamidinobenzylamide×HCl were dissolved in 30 ml of DMF after which 0.33 g (0.634 mmol) of PyBop and 331 µl (1.902 mmol) of DIEA were added at 0° C. The mixture was stirred for 30 min at 0° C and for a further 4 h at room temperature. The solvent was removed in vacuo and the residue was taken up in ethyl acetate; this solution was then washed, in each case 2×, with 5% $KHSO_4$ and NaCl-saturated water, and then dried with $Na_2SO_4$. The solvent was removed in vacuo. There then remained a slightly yellow oil which was used-directly for the next step in the synthesis.

Yield: 0.724 g (oil), HPLC: 38.88% B

8d) Bzls-dSer(tBu)-Arg-4-Amidinobenzylamide×2 Acetate 0.724 g of Bzls-dSer(tBu)-Arg-4-acetyloxamidinobenzylamide (crude product) was dissolved in 30 ml of 90% acetic acid; 100 mg of catalyst (10% Pd/C) were then added to this solution. The mixture was hydrogenated with hydrogen for 6 h at room temperature and under standard pressure. The catalyst was then filtered off, after which the solvent was partially evaporated off and the product was precipitated by adding diethyl ether, filtered off with suction and washed once again with diethyl ether. The white, crystalline precipitate was dried in vacuo.

Yield: 0.367 g (0.508 mmol), HPLC: 31.66% B.

8e) Bzls-dSer-Arg-4-Amidinobenzylamide×2 TFA 5 ml of 90% TFA were added to 140 mg (0.194 mmol) of benzylsulfonyl-dSer(tBu)-Gly-4-amidinobenzylamide×2 AcOH. The mixture was left at room temperature for 60 min and the solvent was then partially evaporated off and the product was precipitated by adding diethyl ether, filtered off with suction and washed once again with diethyl ether. The white, crystalline precipitate was dried in vacuo and purified by means of preparative reversed-phase HPLC.

Yield: 74 mg (0.055 mmol) HPLC: 22.15% B

MS: calculated, 546.65 (monoisotopic). found, 547.34 [M+H]$^+$.

TABLE 3

Inhibition constants ($K_i$ in μM) and elimination (β phase) half-lives ($t_{1/2}$ in h), following the intravenous administration of 1 mg/kg to rats, for inhibitors possessing the general structure. The inhibition constants ($K_i$ and $t_{1/2}$) for uPA were determined as described in Stürzebecher et al., (1997) Vol. 40, 3091-3099, while those for plasmin, trypsin and thrombin were determined in analogy therewith.

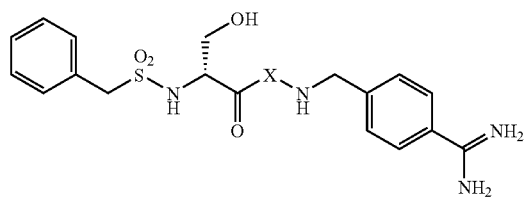

| X | $K_i$ (μm) | | | | $t_{1/2}$ (h) |
| --- | --- | --- | --- | --- | --- |
| | uPA | plasmin | trypsin | thrombin | |
| Lys | 0.024 | 0.36 | 0.0068 | 4.3 | 0.7 |
| Arg | 0.0089 | 0.2 | 0.007 | 4.7 | 0.6 |

EXAMPLE 9

Benzylsulfonyl-dSer-Lys(CO—O-PEG5000-OMe)-4-amidinobenzylamide×Acetate

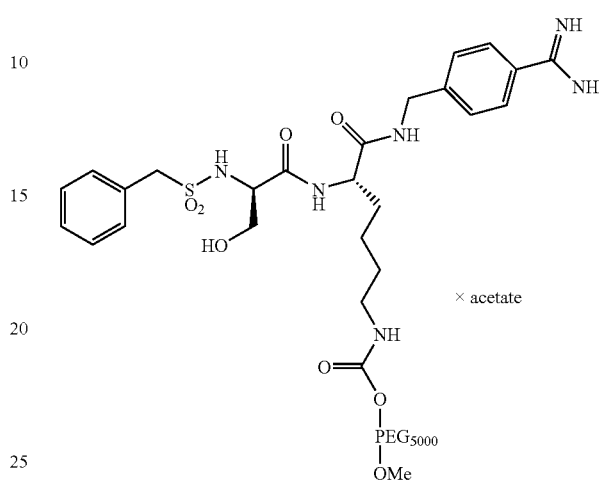

224 mg (0.3 mmol) of benzylsulfonyl-dSer-Lys-4-amidinobenzylamide×2 TFA were dissolved in 20 ml of DMF, after which 1 g (0.2 mmol) of methoxypolyethylene glycol p-nitrophenyl carbonate (molecular weight 5000 Da, Sigma) and 52 μl (0.3 mmol) of DIEA were added at room temperature. After 1 h, a further 20 μl of DIEA were added. After 4 h, the DMF was removed in vacuo and the residue was dissolved in a little methanol; a large volume of isopropanol was then added to this solution, which was then stored in ice. The product which had precipitated out was filtered off with suction and washed on the frit with an ample quantity of isopropanol and then with diethyl ether as well. The crude product (approx. 1 g) was dried in vacuo and purified using an ion exchanger. For this, the crude product was dissolved in water and the solution was loaded onto a column (5 cm×20 cm, Fractogel EMD COO—, equilibrated with water). The column was first of all washed with 1000 ml of water and, after that, the product was eluted using a 2 mM solution of ammonium acetate. The product-containing fractions (HPLC control, elution at 44.96% B) were pooled and the water was partially evaporated off. The product was lyophilized a total of 3× from water.

Yield: 590 mg, HPLC: 44.96% B

| $K_i$ (μm) | | | | $t_{1/2}$ (h) |
| --- | --- | --- | --- | --- |
| uPA | plasmin | trypsin | thrombin | |
| 0.095 | 0.73 | 0.034 | 1.7 | 1.2 |

EXAMPLE 10

Bzls-dSer-Lys(CO—CH$_2$—O—CH$_2$—CO—NH—CH$_2$—CH$_2$-Hexaethylene-glycol-CH$_2$—CH$_2$—NH$_2$)-4-amidinobenzylamide×2 TFA

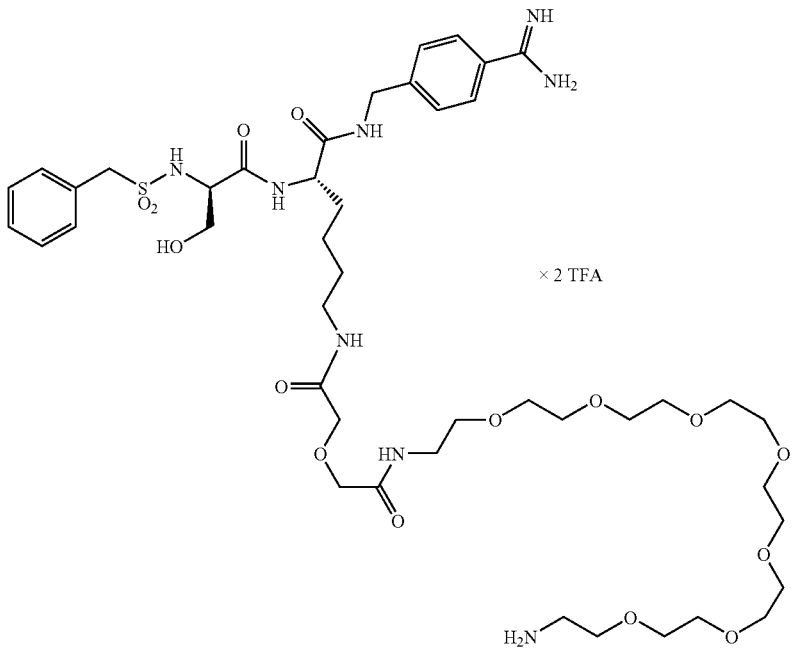

0.392 g (approx. 0.478 mmol) of Bzls-dSer-Lys-4-amidinobenzylamide×2 TFMSA and 280 mg (0.478 mmol) of O-(N-Boc-2-aminoethyl)-0'-(N-diglycolyl)-2-aminoethyl)-hexaethylene glycol (Novabiochem) were dissolved in 15 ml of DMF. 0.249 g (0.478 mmol) of PyBop and 250 μl (1.434 mmol) of DIEA were added while cooling with ice. The mixture was stirred for 15 min while cooling with ice and for a further 4 h at room temperature. After that, the solvent was evaporated off in vacuo and 2 ml of water and 18 ml of TFA were added to the residue. The mixture was stirred at room temperature for 1 h and, after that, the solvent was removed in vacuo. Toluene was added to the residue and the solvent was again removed in vacuo. This procedure was repeated once again. The residue was solubilized in a little methanol and the product was precipitated by adding diethyl ether, filtered off with suction and purified by means of preparative HPLC.

Yield: 245 mg, HPLC: 26.87% B

MS: calculated, 984.48 (monoisotopic). found, 985.6 [M+H]$^+$.

| K$_i$ (μm) | | | | |
|---|---|---|---|---|
| uPA | plasmin | trypsin | thrombin | t$_{1/2}$ (h) |
| 0.042 | 0.53 | 0.0047 | 1.4 | 0.88 |

EXAMPLE 11

Benzylsulfonyl-dDap-Gly-4-Amba

The compound is synthesized using the standard methods known to the skilled person. The inhibition constants are as follows:

| K$_i$ (μm) | | | | |
|---|---|---|---|---|
| uPA | plasmin | trypsin | thrombin | t$_{1/2}$ (h) |
| 0.18 | 9.6 | 0.18 | 10 | n.d. |

EXAMPLE 12

Benzylsulfonyl-dSer-His-4-Amba

The compound is synthesized using the standard methods known to the skilled person. The inhibition constants are as follows:

| K$_i$ (μm) | | | | |
|---|---|---|---|---|
| uPA | plasmin | trypsin | thrombin | t$_{1/2}$ (h) |
| 0.11 | 0.40 | 0.025 | 8.5 | n.d. |

EXAMPLE 13

4(HOOC—CH$_2$)Benzylsulfonyl-dSer-Gly-4-Amba

The compound is synthesized using the standard methods known to the skilled person. The inhibition constants are as follows:

| $K_i$ (μm) | | | | |
| --- | --- | --- | --- | --- |
| uPA | plasmin | trypsin | thrombin | $t_{1/2}$ (h) |
| 0.13 | 27 | 0.3 | 60 | n.d. |

EXAMPLE 14

Inhibiting Metastasis in an Animal Model

The influence of the inhibitor benzylsulfonyl-dSer-Ser-4-amidinobenzylamide on metastasis was investigated in female mice (strain CD1 nu/nu, approx. 25 g body weight, Charles River, Sulzfeld). 10⁶ cells from a lacZ-labeled human fibrosarcoma cell line (HT1080 AN PKZ12 K15-1, dissolved in 200 μl of PBS) were administered to the mice i.v. (Krüger et al., Cancer Metastasis Rev. 1998-99, 17, 285-294 and Krüger et al., Oncogene 1998, 16, 2419-2423). The mice in the treated group (n=17) were given 2 i.p. doses (in each case 1.5 mg/kg) of the inhibitor daily from day −1 (one day before the tumor cell inoculation) through to the 21st day (a total of 23 days). The mice in the control group (n=10) were correspondingly given 200 μl of pyrogen-free water containing 5% (v/v) ethanol. On day 22, the mice were sacrificed and the lungs were fixed in 2% formalin and 0.2% glutaraldehyde; after that, the lungs were stained with X-Gal (5-Br-4-Cl-3-indolyl-β-D-galactoside) and the number of lung metastases was determined.

Result: The number of lung metastases in the group treated with the inhibitor benzylsulfonyl-dSer-Ser-4-amidinobenzylamide was reduced down to 4.6% as compared with the control group (100%).

| Abbreviations employed: | |
| --- | --- |
| Ac | acetyl |
| Boc | tert-butyloxycarbonyl |
| Bzl | benzyl |
| Bzls | benzylsulfonyl |
| Dab | α,γ-diaminobutyric acid |
| Dap | α,β-diaminopropionic acid |
| DIEA | diisopropylethylamine |
| DMF | N,N-dimethylformamide |
| dSer | D-serine |
| IBCC | isobutyl chlorocarbonate |
| Bu | iso-butyl |
| i.v. | in vacuo |
| n.d. | not determined |
| NMM | N-methylmorpholine |
| PyBOP | benzotriazol-1-yl-N-oxytris(pyrrolidino)-phosphonium hexafluorophosphate |
| TEA | triethylamine |
| TFA | trifluoroacetic acid |
| Tfa | trifluoroacetyl |
| TFMSA | trifluoromethanesulfonic acid |
| THF | tetrahydrofuran |

Columns 35-36, claim 12, the following two compounds recited in claim 12 should appear in column 35 instead of column 36,
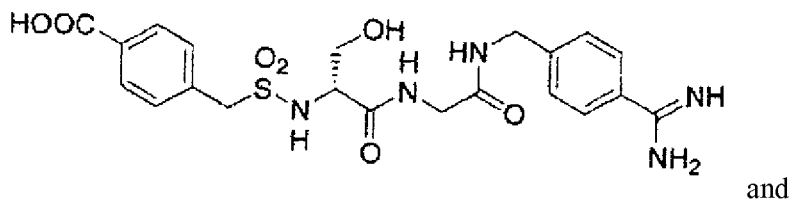 and
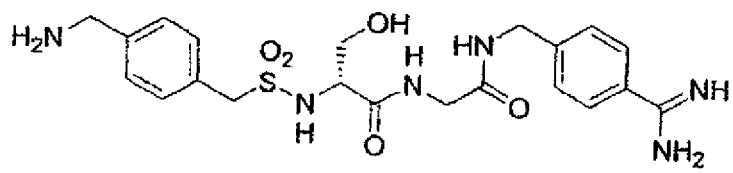

The invention claimed is:

1. A compound of the general formula I

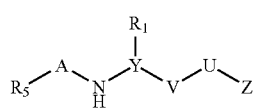

(I)

wherein

A is $P_2$—$P_1$ in which

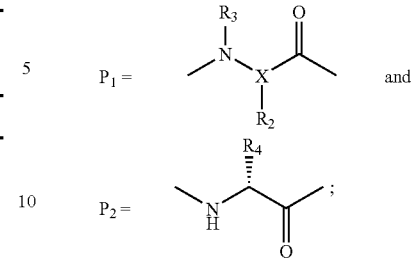

$R_1$ is H or —$(CH_2)_a COOR_6$, in which a=0, 1, 2, 3, 4, or 5, and where $R_6$ is a branched or unbranched alkyl radical having from 1 to 6 C atoms $R_2$ is an H, a branched or unbranched alkyl radical having from 1 to 8 C atoms, or
—$(CH_2)_c COOR_8$, in which c=1, 2, 3, or 4, where $R_8$ is H or a branched or unbranched alkyl radical having from 1 to 6 C atoms or
—$(CH_2)_d$—$OR_9$, in which d=1, 2, 3, or 4, where $R_9$ is H, or
—$(CH_2)_e R_{10}$, —$(CH_2)_e$—$OR_{10}$, —$(CH_2)_e$—$SR_{10}$, —$(CH_2)_e$-guanidino, —$(CH_2)_e$-imidazole or —$(CH_2)_e NHR_{10}$, in which e=1, 2, 3, 4, or 5, where $R_{10}$ is H, a branched or unbranched alkyl radical having 1-16 C atoms, or a substituted or unsubstituted aryl, heteroaryl, aralkyl, or heteroaralkyl radical, where the alkyl radical possesses from 1 to 16 C atoms, and the aryl or heteroaryl radical possesses from 4 to 14 C atoms, and from 1 to 3 N as heteroatom, or —$(CH_2)_k O$—$CO$—$OR_{16}$, in which k=1, 2, 3, 4, 5, 6, 7, or 8, where $R_{16}$ is a branched or unbranched alkyl having 1-16 C atoms, a substituted or unsubstituted aryl, heteroaryl, aralkyl, or heteroaralkyl radical, or an adamantyl, a camphor, or a cyclohexylmethyl radical; and $R_5$ is —$(CH_2)_g(CH_3)_h$, in which g+h=1, 2, or 3, —$(CH_2)_i$-aryl, in which i=0, 1, 2, or 3, —$SO_2 R_{12}$, —$COR_{12}$ or —$COOR_{12}$, where $R_{12}$ is a branched or unbranched alkyl having 1-16, C atoms, a substituted or unsubstituted aryl, heteroaryl, aralkyl, or heteroaralkyl radical, or an adamantyl, a camphor, or a cyclohexylmethyl radical, where $R_5$ is optionally modified with a —$(CH_2)_j COOR_{13}$, —$(CH_2)_j SO_2 R_{13}$, —$(CH_2)_j NH_2$, —$(CH_2)_j$-amidino, —$(CH_2)_j$-hydroxyamidino, or —$(CH_2)_j$-guanidino group in which j=0, 1, or 2, where $R_{13}$ is H or an alkyl radical having from 1 to 6 C atoms; or $R_3$ is H or —$(CH_2)_b R_7$, in which b=1, 2, 3, 4, 5, 6, 7, or 8, where $R_7$ is H, a branched or unbranched alkyl radical having from 1 to 10 C atoms or a —$(CH_2)_j COOR_{13}$, —$(CH_2)_j SO_2 R_{13}$, or —$(CH_2)_j NH_2$, or —$(CH_2)_j$-amidino, —$(CH_2)_j$ hydroxyamidino, or —$(CH_2)_j$-guanidino group in which j=0, 1, or 2, where $R_{13}$ is H or an alkyl radical having from 1 to 6 C atoms, and with $P_1$ being present in the L configuration in the structure A;

$R_4$ is a branched or unbranched alkyl radical having from 1 to 8 C atoms, —$(CH_2)_f OR_{11}$, —$(CH_2)_f SR_{11}$, or —$(CH_2)_f NHR_{11}$ in which f=1, 2, 3, 4, 5, 6, 7, or 8, where $R_{11}$ is H or —$CO$—$OR_{17}$, where $R_{17}$ is a branched or unbranched alkyl having 1-16 C atoms, a substituted or unsubstituted aryl, heteroaryl, aralkyl, or heteroaralkyl radical, or an adamantyl, a camphor, or a cyclohexylmethyl radical and with $P_2$ being present in the D configuration in the structure A;

U is a phenyl or cyclohexyl radical or a heterophenyl or heterocyclohexyl radical having at least one N, S, or O as heteroatom;

V is (CH$_2$)$_n$ in which n is 0, 1, 2, or 3;

X is N or CH;

Y is N or (CH)$_m$ in which m=0 or 1;

Z occurs in the 3 or 4 position and is an aminomethyl, a guanidine, or an amidino group

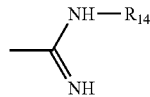

where R$_{14}$ is H, OH, NH$_2$, —COR$_{15}$ or —COOR$_{15}$, where R$_{15}$ is a branched or unbranched alkyl radical having from 1 to 16 C atoms or a substituted or unsubstituted aryl or heteroaryl, aralkyl, or heteroaralkyl radical, where the alkyl radical possesses from 1 to 16 C atoms and the aryl or heteroaryl radical possesses from 4 to 14 C atoms and from 1 to 3 N as heteroatom;

characterized in that one or more radicals, selected from —COOH, —CH(COOH)$_2$, —SO$_2$H, NH$_2$, an amidino, hydroxyamidino, amidrazono, or guanidino group, or a salt thereof, are present in the radicals R$_1$, R$_2$, R$_3$ or R$_5$; or a compound of the general formula I in the form of a prodrug or in the form of its salt.

2. The compound as claimed in claim 1, in which an amino group-functionalized or carboxyl group-functionalized oligo- or polyalkylene glycol chain is coupled directly to a functional group of R$_2$, with the formation of an amide bond at R$_2$, with the oligo- or polyalkylene glycol chain possessing a substituted or unsubstituted amino group and/or carboxyl group, at least at both ends, or with the oligo- or polyalkylene glycol chain possessing a substituted or unsubstituted amino group and/or carboxyl group, at one end and being present, at the other end, as an alkyl ether having 1-4 C atoms, with R$_2$ being (a) —(CH$_2$)$_n$—NH$_2$ in which n is 1-5, or (b) —(CH$_2$)$_n$—COOH in which n is 1-5.

3. The compound as claimed in claim 2, wherein, after coupling the oligo- or polyalkylene glycol, P$_1$ has the general formula II

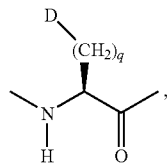

where q is 0, 1, 2, 3, 4, or 5 and D is formula III

E-F-G- (III)

where, when E is an H$_2$N, HOOC—(CH$_2$)$_n$—CO—NH, HOOC, or H$_2$N—(CH$_2$)$_n$—NH—CO group, F is an oligo- or polyalkylene glycol of the general formula —(CH$_2$)$_d$—[O—CH$_2$—CH$_2$]$_v$O—(CH$_2$)$_m$—(NH—CO—CH$_2$—O—CH$_2$)$_k$— or —(CH$_2$)$_d$—[O—CH(CH$_3$)—CH$_2$]$_v$O—(CH$_2$)$_m$—(NH—CO—CH$_2$—O—CH$_2$)$_k$—, in which d=1, 2, 3, or 4, v=an integer from 1 to 1000 m=0, 1, 2, 3, or 4, and k=0 or 1, or, when E is a CH$_3$—O group, F is an oligo- or polyalkylene glycol chain of the general formula —(CH$_2$)$_d$—[O—CH$_2$—CH$_2$]$_v$O—(CH$_2$)$_m$—(NH—CO—CH$_2$—O—CH$_2$)$_k$— or —(CH$_2$)$_d$—[O—CH(CH$_3$)—CH$_2$]$_v$O—(CH$_2$)$_m$—(NH—CO—CH$_2$—O—CH$_2$)$_k$—, in which d=1, 2, 3, or 4, v=an integer from 1 to 1000 m=0, 1, 2, 3, or 4, and k=0 or 1;

and G is —CO—NH— or —NH—CO—.

4. The compound as claimed in claim 1, wherein U is substituted at 1, 2, or 3 positions by a halogen, or a methyl, ethyl, propyl, methoxy, ethoxy, or propoxy radical.

5. The compound as claimed in claim 1, wherein a carboxyl group is protected as an ester.

6. The compound as claimed in claim 1, in the form of a prodrug, with R$_9$ and/or R$_{11}$ in this case being an alkylcarbonyl, aralkylcarbonyl, alkyloxycarbonyl, or aralkoxycarbonyl radical, with the alkyl radical having from 1 to 6 C atoms and the aryl radical having from 5 to 8 C atoms.

7. The compound as claimed in claim 1, characterized in that the amidino group is in the 4 position in the amidinobenzylamide radical and in that P$_2$ is derived from the amino acid D-Ser and P$_1$ is derived from glycine, alanine, serine, aspartic acid or glutamic acid, and in that R$_5$ is an unsubstituted aryl- or aralkylsulfonyl radical, or such a radical provided with a carboxyl group or carboxyalkyl group, having from 1 to 16 C atoms in the alkyl radical and from 6 to 14 C atoms in the aryl radical.

8. The compound as claimed in claim 1, characterized in that the amidino group is in the 4 position in the amidinobenzylamide radical and in that P2 is the amino acid D-Ser and P1 is a natural or artificial, unsubstituted or substituted, basic amino acid in the L configuration selected from the group consisting of Lys, homoLys, Arg, norArg, homoArg, His, Orn, Orn(2-imidazolinyl), Dab, 4-[(2-amino)pyrimidinyl]butyric acid, Dap, Ala[3-(2-pyrrolidinyl)], Ala[3-pyrrolidinyl-(2-N-amidino)], Ala[3-(N-piperazine-4-N-amidino], Ala(4-Pip), Ala[4-Pip(N-amidino)], homoAla(4-Pip), Ala[3-Pip (N-amidino)], homoAla(3-Pip), homoAla[4-Pip(N-amidino) ], Ala-(3-guanidino), Phe(3-amidino), Phe(4-amidino), Phe(3-NH$_2$), Phe(4-NH$_2$), Phe(3-guanidino), Phe(4-guanidino), Phe[4-(2-imidazolinyl)], Phe[3-CH$_2$-(guanidine)], Phe[4-CH$_2$-(guanidino)], homoPhe(3-amidino), homoPhe(4-amidino), hPhe(3-NH$_2$), hPhe(4-NH$_2$), hPhe(3-guanidino), hPhe(4-guanidino), cis-Cha(4-NH$_2$), trans-Cha (4-NH$_2$), cis-homoCha(4-NH$_2$), trans-homoCha(4-NH$_2$), trans-Cha (4-CH$_2$NH$_2$), and trans-homoCha(4-CH$_2$NH$_2$), and in that R$_5$ is a sulfonyl group-provided aryl- or aralkylsulfonyl radical having from 1 to 16 C atoms in the alkyl radical and from 6 to 14 C atoms in the aryl radical, which is bonded to the amino group of the D-Ser.

9. The compound as claimed in claim 8, characterized in that P1 is the amino acid Lys or Arg.

10. The compound as claimed in claim 1, characterized in that the substituent on the substituted aryl, heteroaryl, aralkyl, or heteroaralkyl radical is a halogen.

11. The compound as claimed in claim 1, characterized in that a compound of the general formula I has the following structure:

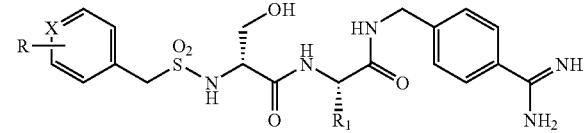

in which R is COOH, HOOC—(CH$_2$)$_p$— or R$_{18}$OOC—(CH$_2$)$_p$— in which p=1 and 2 and R$_{18}$=methyl or ethyl, or COOMe in ortho, meta or para, or H, and X is CH and R$_1$ is H; or R is 4-COOH or 3-COOH, with X being CH and R$_1$ being H, CH$_3$ or CH$_2$—OH; or R is 4-CN, with X being CH and $R_1$ being $CH_3$; or R is 4-($NH_2$—$CH_2$), with X being CH and $R_1$ being H; or R is 4-COOMe, with X being CH and $R_1$ being $CH_2$—OH.

12. The compound as claimed in claim 1, characterized in that a compound of the general formula I has one of the following structures:

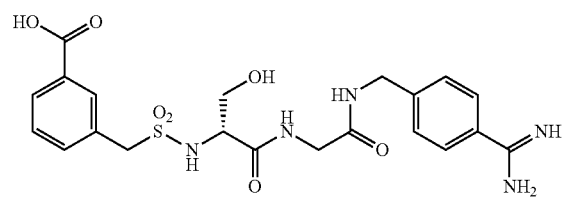

or

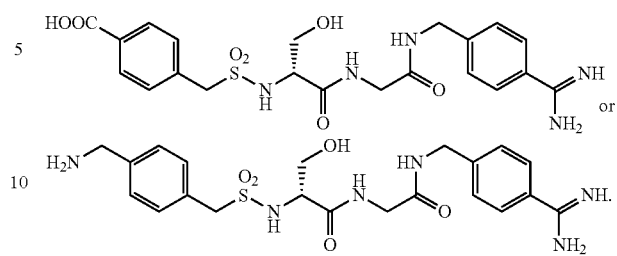

or

13. The compound as claimed in claim 1, characterized in that a compound of the general formula I has one of the following structures:

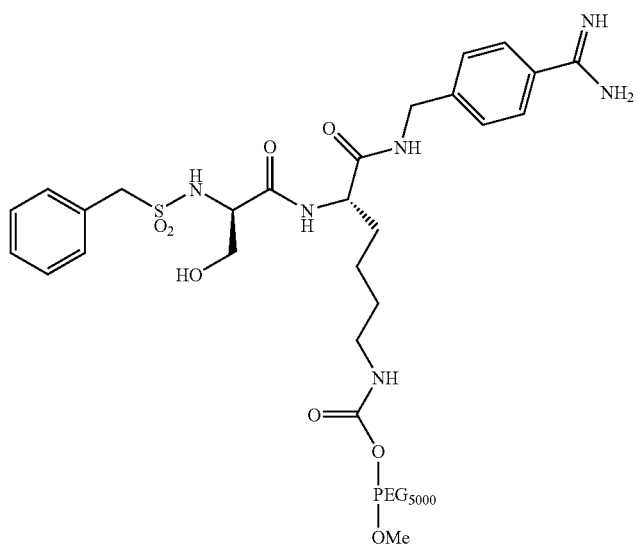

or

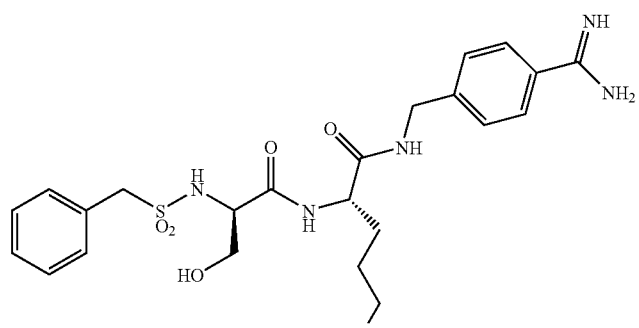

-continued

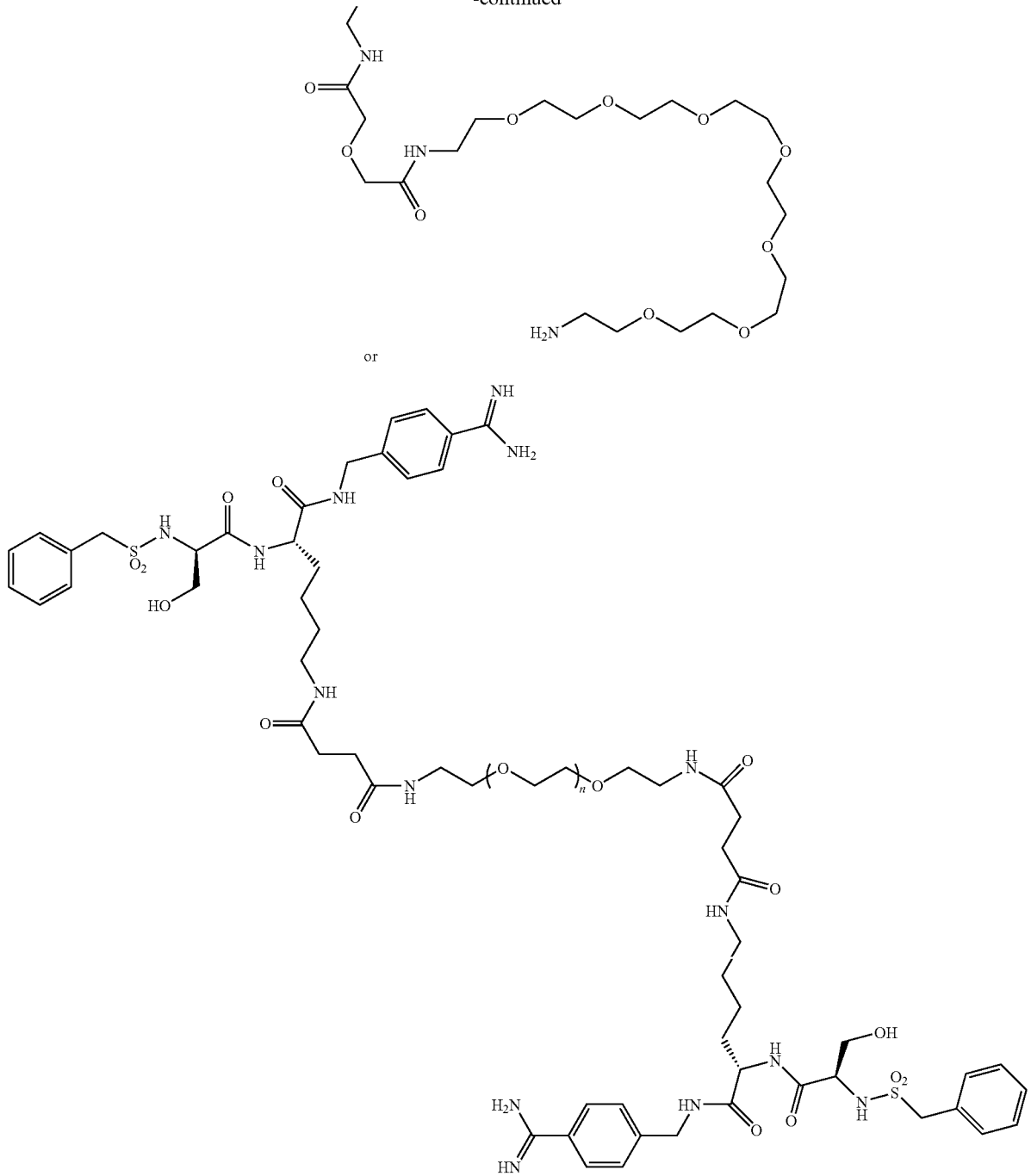

in which n=2 to 250.

14. The compound as claimed in claim 1, characterized in that the compounds are mineral acid or organic acid salts.

15. The compound as claimed in claim 14, characterized in that said salts are sulfates, acetic acid, formic acid, methylsulfonic acid, succinic acid, malic acid, or trifluoroacetic acid.

16. A process for preparing a compound as claimed in claim 1, the process comprising sequentially coupling the appropriate amino acids to a 4-acetyloxamidinobenzylamine, with either the N-terminal amino acid already carrying the $R_5$ radical or with this radical subsequently being bonded to it.

17. A pharmaceutical composition comprising a compound as claimed in claim 1 and pharmaceutically suitable auxiliary substances and/or additives.

18. The pharmaceutical composition as claimed in claim 17, wherein the pharmaceutical composition is used in the form of a tablet, a sugar-coated tablet, a capsule, a pellet, a suppository, a solution, an injection solution or infusion solution, eyedrops, nose drops and ear drops, a juice, an emulsion or suspension, a globule, a stylus, an aerosol, a powder, a paste, a cream or an ointment.

19. The compound as claimed in claim 1 being benzylsulfonyl-dSer-Arg-4-amidinobenzylamide.

20. The compound of claim 1, wherein characterized in that one or more radicals selected from —COOH, —CH(COOH)$_2$, —SO$_2$H, NH$_2$, an amidino, hydroxyamidino, amidrazono, or guanidino group, is present in the radicals R$_1$, R$_2$, R$_3$ or R$_5$.

21. The compound of claim 1, wherein the salt of one or more radicals selected from —COOH, —CH(COOH)$_2$, —SO$_2$H, NH$_2$, an amidino, hydroxyamidino, amidrazono, or guanidino group, is present in the radicals R$_1$, R$_2$, R$_3$ or R$_5$.

* * * * *

UNITED STATES PATENT AND TRADEMARK OFFICE
CERTIFICATE OF CORRECTION

| | | |
|---|---|---|
| PATENT NO. | : 7,838,560 B2 | Page 1 of 3 |
| APPLICATION NO. | : 10/506579 | |
| DATED | : November 23, 2010 | |
| INVENTOR(S) | : Stürzebecher et al. | |

It is certified that error appears in the above-identified patent and that said Letters Patent is hereby corrected as shown below:

Title Page, Under FOREIGN APPLICATION PRIORITY DATA, replace
"102 45 059" with --102 45 059.5--;

Under FOREIGN APPLICATION PRIORITY DATA, replace
"102 61 435" with --102 61 435.0--.

Column 1, Line 29, replace "uPa" with --uPA--;
        Line 46, replace "UPAR" with --uPAR--.

Column 11, Line 38, replace "($P_2$)" with --(P2)--.

Column 18, Line 52, replace "(monoisotopic). found," with --(monoisotopic), found,--.

Column 20, Line 29, replace "Ser." with --Ser--.

Column 22, Line 21, replace "(monoisotopic). found," with --(monoisotopic), found,--;

Line 34, replace "(monoisotopic). found," with --(monoisotopic), found,--;

Line 45, replace "(monoisotopic). found," with --(monoisotopic), found,--.

Column 25, Line 5, replace "axcetyloxamidinobenzylamide" with --acetyloxamidinobenzylamide--.

Column 27, Line 33, replace "(monoisotopic). found," with --(monoisotopic), found,--.

Signed and Sealed this
Seventh Day of August, 2012

David J. Kappos
*Director of the United States Patent and Trademark Office*

CERTIFICATE OF CORRECTION (continued)
U.S. Pat. No. 7,838,560 B2

Column 27, lines 50-55, the structure

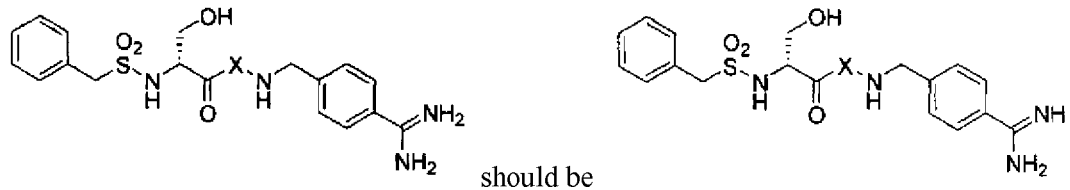 should be

Column 28, lines 10-25, the structure

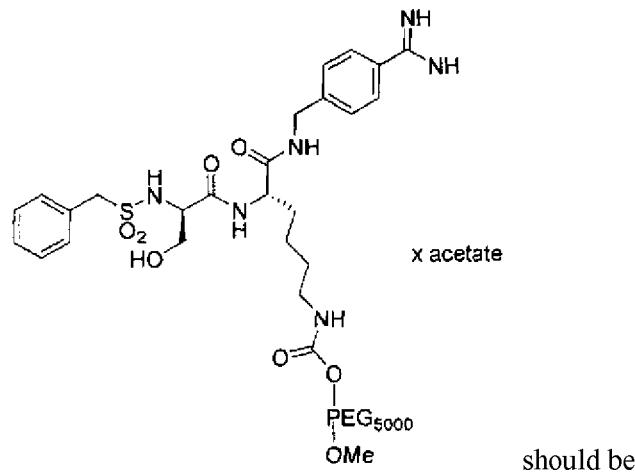 should be

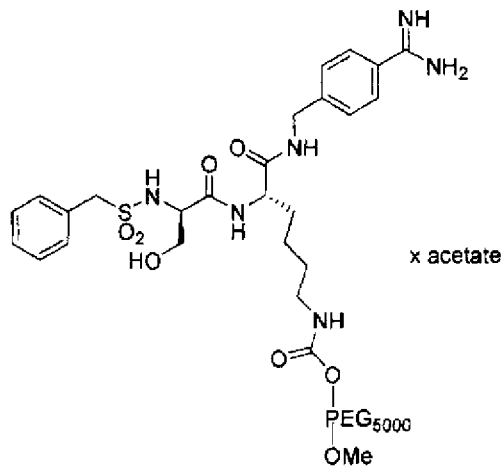

Column 29, Line 51, replace "(monoisotopic). found," with --(monoisotopic), found,--.

Column 34, Lines 37-38, claim 8, replace "Phe[3-CH$_2$-(guanidine)]" with
--Phe[3-CH$_2$-(guanidino)]--.